(12) United States Patent
Marquis et al.

(10) Patent No.: US 6,369,077 B1
(45) Date of Patent: Apr. 9, 2002

(54) PROTEASE INHIBITORS

(75) Inventors: Robert W. Marquis, St. Davids; Yu Ru, Havertown; Daniel F. Veber, Ambler; Stephen M. LoCastro, Exton, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/423,325

(22) PCT Filed: May 6, 1998

(86) PCT No.: PCT/US98/09192

§ 371 Date: Nov. 4, 1999

§ 102(e) Date: Nov. 4, 1999

(87) PCT Pub. No.: WO98/50534

PCT Pub. Date: Nov. 12, 1998

Related U.S. Application Data

(60) Provisional application No. 60/046,865, filed on May 8, 1997.

(51) Int. Cl.$^7$ .................. A61K 31/445; A61K 31/40; C07D 211/56; C07D 207/10

(52) U.S. Cl. .................. 514/315; 514/423; 514/426; 546/244; 548/530; 548/557

(58) Field of Search ................. 548/530, 557; 546/244; 514/315, 423, 426

(56) References Cited

U.S. PATENT DOCUMENTS

| | | | |
|---|---|---|---|
| 4,212,866 A | 7/1980 | Friebe et al. | |
| 4,301,151 A | 11/1981 | Veber et al. | 424/177 |
| 4,443,461 A | 4/1984 | Ward | |
| 4,680,283 A | 7/1987 | Veber et al. | 514/17 |
| 5,514,694 A | 5/1996 | Powers et al. | 514/357 |

FOREIGN PATENT DOCUMENTS

| | | |
|---|---|---|
| EP | 0 008 014 A1 | 7/1979 |
| EP | 0 354 568 A2 | 8/1989 |
| EP | 0 416 581 A1 | 9/1990 |
| EP | 0 480 044 A1 | 3/1991 |
| WO | WO 94/27967 | 12/1994 |
| WO | WO 96/40741 | 12/1996 |
| WO | WO 98/05336 | 2/1998 |

OTHER PUBLICATIONS

CA 126:60362, abstract of WO9635713, 1996, Carpino.*
Yamashita et al., "Structure and Design of Potent and Selective Cathepsin K Inhibitors", *J. Am. Chem. Soc.*, 119, pp. 11351–11352 (1997).
Tsuda et al., "Postsatin, a New Inhibitor of Prolyl Endopeptidase, VI.", *Journal of Antibiotics*, 49(9), pp. 900–908 (1996).
Tsuda et al., "Postsatin, a New Inhibitor of Prolyl Endopeptidase, VII.", *Journal of Antibiotics*, 49(9), pp. 909–920 (1996).

* cited by examiner

Primary Examiner—D. Margaret Seaman
(74) Attorney, Agent, or Firm—Mary E. McCarthy; Stephen Venetianer; Charles M. Kinzig

(57) ABSTRACT

This invention relates to compounds of formula (I):

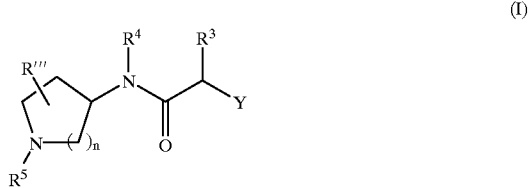

wherein:

Y is Ar or $NR^1R^2$;

$R^1$ is R", R"C(O), R"C(S), R"SO$_2$, R"OC(O), R"R'NC(O), or R"R'NC(S);

$R^2$ is H, C$_{1-6}$alkyl, C$_{2-6}$alkenyl, Ar-C$_{0-6}$alkyl, or Het-C$_{0-6}$alkyl;

$R^3$ is H, C$_{2-6}$alkenyl, C$_{2-6}$alkynyl, Het, Ar or C$_{1-6}$alkyl optionally substituted by OR', SR', NR'$_2$, N(R')C(O)OR", CO$_2$R', CO$_2$NR'$_2$, N(C=NH)NH$_2$, Het or Ar;

$R^4$ is H, C$_{1-6}$alkyl, C$_{2-6}$alkenyl, Ar-C$_{0-6}$alkyl, or Het-C$_{0-6}$alkyl;

$R^5$ is

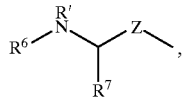

Ar-C$_{0-6}$alkyl, Het-C$_{0-6}$alkyl, adamantyl-C(O)—, Ar-C(O)—, Het-C(O)— or;

$R^6$ is R", R"C(O), R"C(S), R"SO$_2$, R"OC(O), R"R'NC(O), R"R'NC(S), or R"OC(O)NR'CH(R*)C(O);

$R^7$ is C$_{3-6}$cycloalkyl-C$_{0-6}$alkyl, Ar-C$_{0-6}$alkyl, Het-C$_{0-6}$alkyl, Ar-C$_{0-6}$alkoxy, Het-C$_{0-6}$alkoxy, or C$_{1-6}$alkyl optionally substituted by OR', SR', NR'$_2$, N(R')C(O)OR", CO$_2$R', CO$_2$NR'$_2$, N(C=NH)NH$_2$, Het or Ar;

R* is H, C$_{1-6}$alkyl, C$_{2-6}$alkenyl, C$_{3-6}$cycloalkyl-C$_{0-6}$alkyl, Ar-C$_{0-6}$alkyl, Het-C$_{0-6}$alkyl;

each R' independently is H, C$_{1-6}$alkyl, C$_{2-6}$alkenyl, Ar-C$_{0-6}$alkyl, or Het-C$_{0-6}$alkyl;

each R" independently is C$_{1-6}$alkyl, C$_{3-6}$cycloalkyl-C$_{0-6}$alkyl, Ar-C$_{0-6}$alkyl, or Het-C$_{0-6}$alkyl;

R'" is H, C$_{1-6}$alkyl, C$_{3-6}$cycloalkyl-C$_{0-6}$alkyl, Ar-C$_{0-6}$alkyl, or Het-C$_{0-6}$alkyl;

Z is C(O) or CH$_2$; and n is 1, 2 or 3;

or a pharmaceutically acceptable salt thereof, which are inhibitors of cysteine proteases, particularly cathepsin K, and are useful in the treatment of diseases in which inhibition of bone loss is a factor.

23 Claims, No Drawings

PROTEASE INHIBITORS

This is a 371 of PCT/US98/09192, filed May 6, 1998 which claims benefit of Provisional Application No. 60/046,865, filed May 8, 1997.

FIELD OF THE INVENTION

This invention relates to novel protease inhibitors, particularly inhibitors of cysteine and serine proteases, more particularly compounds which inhibit cysteine proteases, even more particularly compounds which inhibit cysteine proteases of the papain superfamily, yet more particularly compounds which inhibit cysteine proteases of the cathepsin family, most particularly compounds which inhibit cathepsin K. Such compounds are particularly useful for treating diseases in which cysteine proteases are implicated, especially diseases of excessive bone or cartilage loss, e.g., osteoporosis, periodontitis, and arthritis.

BACKGROUND OF THE INVENTION

Cathepsin K is a member of the family of enzymes which are part of the papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein). Cathepsin K has been recently expressed, purified, and characterized. Bossard, M. J., et al., (1996) *J. Biol. Chem.* 271, 12517–12524; Drake, F. H., et al., (1996) *J. Biol. Chem.* 271, 12511–12516; Bromme, D., et al., (1996) *J. Biol. Chem.* 271, 2126–2132.

Cathepsin K has been variously denoted as cathepsin O, cathepsin X or cathepsin O2 in the literature. The designation cathepsin K is considered to be the more appropriate one (name assigned by Nomenclature Committee of the International Union of Biochemistry and Molecular Biology).

Cathepsins of the papain superfamily of cysteine proteases function in the normal physiological process of protein degradation in animals, including humans, e.g., in the degradation of connective tissue. However, elevated levels of these enzymes in the body can result in pathological conditions leading to disease. Thus, cathepsins have been implicated in various disease states, including but not limited to, infections by pneumocystis carinii, trypsanoma cruzi, trypsanoma brucei brucei, and *Crithidia fusiculata;* as well as in schistosomiasis malaria, tumor metastasis, metachromatic leukodystrophy, muscular dystrophy, amytrophy, and the like. See International Publication Number WO 94/04172, published on Mar. 3, 1994, and references cited therein. See also European Patent Application EP 0 603 873 A1, and references cited therein. Two bacterial cysteine proteases from *P. gingivallis,* called gingipains, have been implicated in the pathogenesis of gingivitis. Potempa, J., et al. (1994) *Perspectives in Drug Discovery and Design,* 2, 445–458.

Cathepsin K is believed to play a causative role in diseases of excessive bone or cartilage loss. Bone is composed of a protein matrix in which spindle- or plate-shaped crystals of hydroxyapatite are incorporated. Type I Collagen represents the major structural protein of bone comprising approximately 90% of the structural protein. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodeling at discrete foci throughout life. These foci, or remodeling units, undergo a cycle consisting of a bone resorption phase followed by a phase of bone replacement.

Bone resorption is carried out by osteoclasts, which are multinuclear cells of hematopoietic lineage. The osteoclasts adhere to the bone surface and form a tight sealing zone, followed by extensive membrane ruffling on their apical (i.e., resorbing) surface. This creates an enclosed extracellular compartment on the bone surface that is acidified by proton pumps in the ruffled membrane, and into which the osteoclast secretes proteolytic enzymes. The low pH of the compartment dissolves hydroxyapatite crystals at the bone surface, while the proteolytic enzymes digest the protein matrix. In this way, a resorption lacuna, or pit, is formed. At the end of this phase of the cycle, osteoblasts lay down a new protein matrix that is subsequently mineralized. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

It now has been discovered that a novel class of compounds are protease inhibitors, most particularly inhibitors of cathepsin K, and these compounds are useful for treating diseases in which inhibition of bone resorption is indicated, such as osteoporosis and periodontal disease.

SUMMARY OF THE INVENTION

An object of the present invention is to provide protease inhibitors, particularly such inhibitors of cysteine and serine proteases, more particularly such compounds which inhibit cysteine proteases, even more particularly such compounds which inhibit cysteine proteases of the papain superfamily, yet more particularly such compounds which inhibit cysteine proteases of the cathepsin family, most particularly such compounds which inhibit cathepsin K, and which are useful for treating diseases which may be therapeutically modified by altering the activity of such proteases.

Accordingly, in the first aspect, this invention provides a compound according to formula (I).

In another aspect, this invention provides a pharmaceutical composition comprising a compound according to formula (I) and a pharmaceutically acceptable carrier.

In yet another aspect, this invention provides a method of treating diseases in which the disease pathology may be therapeutically modified by inhibiting proteases, particularly cysteine and serine proteases, more particularly cysteine proteases, even more particularly cysteine proteases of the papain superfamily, yet more particularly cysteine proteases of the cathepsin family, most particularly cathepsin K.

In a particular aspect, the compounds of this invention are especially useful for treating diseases characterized by bone loss, such as osteoporosis and gingival diseases, such as gingivitis and periodontitis, or by excessive cartilage or matrix degradation, such as osteoarthritis and rheumatoid arthritis.

DETAILED DESCRIPTION OF THE INVENTION

The present invention provides compounds of formula (I):

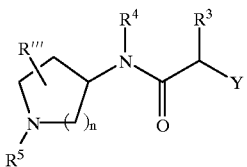

(I)

wherein:

Y is Ar or $NR^1R^2$;

$R^1$ is R", R"C(O), R"C(S), R"SO$_2$, R"OC(O), R"R'NC(O), or R"R'NC(S);

$R^2$ is H, $C_{1-6}$alkyl, $C_{2-6}$alkenyl, Ar-$C_{0-6}$alkyl, or Het-$C_{0-6}$alkyl;

$R^3$ is H, $C_{2-6}$alkenyl, $C_{2-6}$alkynyl, Het, Ar or $C_{1-6}$alkyl optionally substituted by OR', SR', NR'$_2$, N(R')C(O)OR", CO$_2$R', CO$_2$NR'$_2$, N(C=NH)NH$_2$, Het or Ar;

$R^4$ is H, $C_{1-6}$alkyl, $C_{2-6}$alkenyl, Ar-$C_{0-6}$alkyl, or Het-$C_{0-6}$alkyl;

$R^5$ is

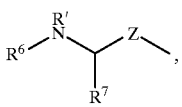

Ar-$C_{0-6}$alkyl, Het-$C_{0-6}$alkyl, adamantyl-C(O)—, Ar-C(O)—, or Het-C(O)—;

$R^6$ is R", R"C(O), R"C(S), R"SO$_2$, R"OC(O), R"R'NC(O), R"R'NC(S),or R"OC(O)NR'CH(R*)C(O);

$R^7$ is $C_{3-6}$cycloalkyl-$C_{0-6}$alkyl, Ar-$C_{0-6}$alkyl, Het-$C_{0-6}$alkyl, Ar-$C_{0-6}$alkoxy, Het-$C_{0-6}$alkoxy, or $C_{1-6}$alkyl optionally substituted by OR', SR', NR'$_2$, N(R')C(O)OR", CO$_2$R', CO$_2$NR'$_2$, N(C=NH)NH$_2$, Het or Ar;

R* is H, $C_{1-6}$alkyl, $C_{2-6}$alkenyl, $C_{3-6}$cycloalkyl-$C_{0-6}$-alkyl, Ar-$C_{0-6}$alkyl, Het-$C_{0-6}$alkyl;

each R' independently is H, $C_{1-6}$alkyl, $C_{2-6}$alkenyl, Ar-$C_{0-6}$ alkyl, or Het-$C_{0-6}$alkyl;

each R" independently is $C_{1-6}$alkyl, $C_{3-6}$cycloalkyl-$C_{0-6}$-alkyl, Ar-$C_{0-6}$alkyl, or Het-$C_{0-6}$alkyl;

R'" is H, $C_{1-6}$alkyl, $C_{3-6}$cycloalkyl-$C_{0-6}$alkyl, Ar-$C_{0-6}$alkyl, or Het-$C_{0-6}$alkyl;

Z is C(O) or CH$_2$; and n is 1, 2 or 3;

or a pharmaceutically acceptable salt thereof.

Preferably, the present invention provides compounds of formula (Ia):

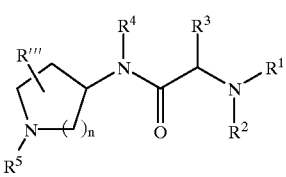

(Ia)

wherein:

$R^1$ is R", R"C(O), R"C(S), R"SO$_2$, R"OC(O), R"R'NC(O), or R"R'NC(S);

$R^2$ is H, $C_{1-6}$alkyl, $C_{2-6}$alkenyl, Ar-$C_{0-6}$alkyl, or Het-$C_{0-6}$alkyl;

$R^3$ is H, $C_{2-6}$alkenyl, $C_{2-6}$alkynyl, Het, Ar or $C_{1-6}$alkyl optionally substituted by OR', SR', NR'$_2$, N(R')C(O)OR", CO$_2$R', CO$_2$NR'$_2$, N(C=NH)NH$_2$, Het or Ar;

$R^4$ is H, $C_{1-6}$alkyl, $C_{2-6}$alkenyl, Ar-$C_{0-6}$alkyl, or Het-$C_{0-6}$alkyl;

$R^5$ is

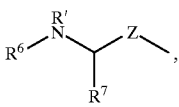

Ar-$C_{0-6}$alkyl, Het-$C_{0-6}$alkyl, adamantyl-C(O)—, Ar-C(O)—, or Het-C(O)—;

$R^6$ is R", R"C(O), R"C(S), R"SO$_2$, R"OC(O), R"R'NC(O), R"R'NC(S),or R"OC(O)NR'CH(R*)C(O);

$R^7$ is $C_{3-6}$cycloalkyl-$C_{0-6}$alkyl, Ar-$C_{0-6}$alkyl, Het-$C_{0-6}$alkyl, Ar-$C_{0-6}$alkoxy, Het-$C_{0-6}$alkoxy, or $C_{1-6}$alkyl optionally substituted by OR', SR', NR'$_2$, N(R')C(O)OR", CO$_2$R', CO$_2$NR'$_2$, N(C=NH)NH$_2$, Het or Ar;

R* is H, $C_{1-6}$alkyl, $C_{2-6}$alkenyl, $C_{3-6}$cycloalkyl-$C_{0-6}$-alkyl, Ar-$C_{0-6}$alkyl, Het-$C_{0-6}$alkyl;

each R' independently is H, $C_{1-6}$alkyl, $C_{2-6}$alkenyl, Ar-$C_{0-6}$ alkyl, or Het-$C_{0-6}$alkyl;

each R" independently is $C_{1-6}$alkyl, $C_{3-6}$cycloalkyl-$C_{0-6}$-alkyl, Ar-$C_{0-6}$alkyl, or Het-$C_{0-6}$alkyl;

R'" is H, $C_{1-6}$alkyl, $C_{3-6}$cycloalkyl-$C_{0-6}$alkyl, Ar-$C_{0-6}$alkyl, or Het-$C_{0-6}$alkyl;

Z is C(O) or CH$_2$; and n is 1, 2 or 3;

or a pharmaceutically acceptable salt thereof.

The present invention includes all hydrates, solvates, complexes and prodrugs of the compounds of this invention. Prodrugs are any covalently bonded compounds which release the active parent drug according to formula (I) in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in formula (I) or any subformula thereof is independent of its meaning, or any other substituent's meaning, at any other occurrence, unless specified otherwise.

With respect to formula (I):

Suitably, $R^4$ and $R'''$ are each H and $R^3$ is $C_{1-6}$alkyl or $C_{2-6}$alkenyl. Preferably, $R^3$ is i-butyl.

Suitably, $R^5$ is benzyl or

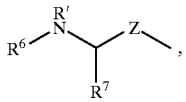

in which R'is H, $R^7$ is $C_{1-6}$alkyl, preferably i-butyl, $R^6$ is R"OC(O), wherein R" is benzyl, and Z is $CH_2$.

Suitably, Y is $NR^1R^2$, in which $R^2$ is H and $R^1$ is R"C(O) or R"OC(O), and R" in said $R^1$ group is $C_{1-6}$alkyl, Ar-$C_{0-6}$alkyl or Het-$C_{0-6}$alkyl, and, most preferably, R" is tert-butyl,

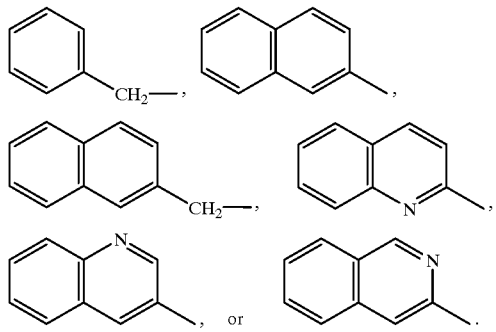

Suitably, n is 1 or 2. Preferably, n is 1.

In one particular embodiment, the formula (Ia) compound of this invention is a compound of formula (Ib):

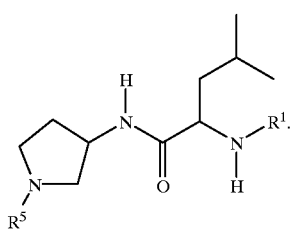

(Ib)

In another embodiment, the formula (Ia) compound of this invention is a compound of formula (Ic):

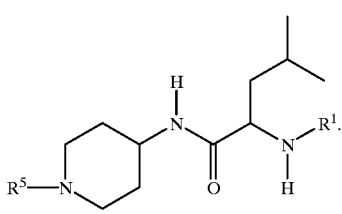

(Ic)

Specific representative compounds of this invention are:

3-[[$N^\alpha$-(2-quinolinecarbonyl)-L-leucinyl]amino]-1-[(2S)-4-methyl-2-[[(benzyloxycarbonyl)amino]pentyl]-pyrrolidine;
1-benzyl-3-[[$N^\alpha$-(2quinolinecarbonyl)-L-leucinyl]amino]-pyrrolidine;
3-[[$N^\alpha$-(2-naphthylcarbonyl)-L-leucinyl]amino]-1-[(2S)-4-methyl-2-[[(benzyloxycarbonyl)amino]pentyl]-pyrrolidine;
1-benzyl-3-[[$N^\alpha$-(2-naphthylcarbonyl)-L-leucinyl]amino]-pyrrolidine;
1-benzyl-(3S)-[[$N^\alpha$-(benzyloxycarbonyl)-L-leuciny]amino]-pyrrolidine;
1-benzyl-(3S)-[[$N^\alpha$-(tert-butoxycarbonyl)-L-leucinyl]amino]-pyrrolidine;
(3S)-[[$N^\alpha$-(2-naphthylcarbonyl)-L-leucinyl]amino]-1-[(2S)-4-methyl-2-[[(benzyloxycarbonyl)amino]pentyl]-pyrrolidine;
(3R)-[[$N^\alpha$-(2-naphthylcarbonyl)-L-leucinyl]amino]-1-[(2S)-4-methyl-2-[[(benzyloxycarbonyl)amino]pentyl]-pyrrolidine;
1-benzyl-(3R)-[[$N^\alpha$-(2-naphthyl)acetyl-L-leucinyl]amino]-pyrrolidine;
1-benzyl-(3R)-[[$N^\alpha$-(2-naphtylcarbonyl)-L-leucinyl]amino]-pyrrolidine;
1-benzyl-(3R)-[[$N^\alpha$-(3-quinolinecarbonyl)-L-leucinyl]amino]-pyrrolidine;
1-benzyl-(3R)-[[$N^\alpha$-(2-quinolinecarbonyl)-L-leucinyl]amino]-pyrrolidine;
1-benzyl-(3R)-[[$N^\alpha$-(3-isoquinolinecarbonyl)-L-leucinyl]amino]-pyrrolidine;
1-benzyl-(3S)-[[$N^\alpha$-(2-naphthyl)acetyl-L-leucinyl]amino]-pyrrolidine;
1-benzyl-(3S)-[[$N^\alpha$-(2-naphthylcarbonyl)-L-leucinyl]amino]-pyrrolidine;
1-benzyl-(3S)-[[$N^\alpha$-(3-quinolinecarbonyl)-L-leucinyl]amino-pyrrolidine;
1-benzyl-(3S)-[[$N^\alpha$-(2-quinolinecarbonyl)-L-leucinyl]amino]-pyrrolidine;
1-benzyl-(3S)-[[$N^\alpha$-(3-isoquinolinecarbonyl)-L-leucinyl]amino]-pyrrolidine;
1-benzyl-4-[[$N^\alpha$-(2-naphthylcarbonyl)-L-leucinyl]amino]-piperidine;
1-benzyl-4-[[$N^\alpha$-(2-quinolinecarbonyl)-L-leucinyl]amino]-piperidine;
1-benzyl-4-[[$N^\alpha$-(benzyloxycarbonyl)-L-leucinyl]amino]-piperidine;
1-[3-(2-pyridyl)phenyl]-2-ethyl-(3S)-[[$N^\alpha$-(2-naphthylcarbonyl)-L-leucinyl]amino]-pyrrolidine;
1-[3-(2-pyridyl)phenyl]-2-ethyl-(3S)-[[$N^\alpha$-(2-quinolinecarbonyl)-L-leucinyl]amino]-pyrrolidine;
1-[3-(2-pyridyl)phenyl]-2-ethyl-(3S)-[[$N^\alpha$-(3-isoquinolinecarbonyl)-L-leucinyl]amino]-pyrrolidine;
1-[3-(2-pyridyl)phenyl]-2-ethyl-(3R)-[[$N^\alpha$-(2-naphthylcarbonyl)-L-leucinyl]amino]-pyrrolidine;
1-[3-(2-pyridyl)phenyl]-2-ethyl-(3R)-[[$N^\alpha$-(3-isoquinolinecarbonyl)-L-leucinyl]amino]-pyrrolidine;
1-[3-(2-pyridyl)phenyl]-2-ethyl-(3R)-[[$N^\alpha$-(2-quinolinecarbonyl)-L-leucinyl]amino]-pyrrolidine;
1-(1-adamantanecarbonyl)-(3R)-[[$N^\alpha$-(4-pyridylmethoxycarbonyl)-L-leucinyl]amino]-pyrrolidine;
1-(1-adamantanecarbonyl)-(3S)-[[$N^\alpha$-(4-pyridylmethoxycarbonyl)-L-leucinyl]amino]-pyrrolidine;
(3R)-[[$N^\alpha$-(benzo[b]thiophene-2-carbonyl)-L-leucinyl]amino]-1-[(2S)-4-methyl-2-[[(benzyloxycarbonyl)amino]pentyl]-pyrrolidine;

(3R)-[[N$^\alpha$-(3,4-dimethoxybenzoyl)-L-leucinyl]amino]-1-[(2S)-4-methyl-2-[[(benzyloxycarbonyl)amino]pentyl]-pyrrolidine;
(3R)-[[N$^\alpha$-(benzofuran-2-carbonyl)-L-leucinyl]amino]-1-[(2S)-4-methyl-2-[[(benzyloxycarbonyl)amino]pentyl]-pyrrolidine;
(3R)-[[N$^\alpha$-(benzothiazole-6-carbonyl)-L-leucinyl]amino]-1-[(2S)-4-methyl-2-[[(benzyloxycarbonyl)amino]pentyl]-pyrrolidine;
(3R)-[[N$^\alpha$-(indole-2-carbonyl)-L-leucinyl]amino]-1-[(2S)-4-methyl-2-[[(benzyloxycarbonyl)amino]pentyl]-pyrrolidine;
(3R)-[[N$^\alpha$-(4-fluorobenzoyl)-L-leucinyl]amino]-1-[(2S)-4-methyl-2-[[(benzyloxycarbonyl)amino]pentyl]-pyrrolidine;
(3R)-[[N$^\alpha$-(4-methoxybenzoyl)-L-leucinyl]amino]-1-[(2S)-4-methyl-2-[[(benzyloxycarbonyl)amino]pentyl]-pyrrolidine;
(3R)-[[N$^\alpha$-(3,4-dichlorobenzoyl)-L-leucinyl]amino]-1-[(2S)-4-methyl-2-[[(benzyloxycarbonyl)amino]pentyl]-pyrrolidine;
(3R)-[[N$^\alpha$-(thiophene-2-carbonyl)-L-leucinyl]amino]-1-[(2S)-4-methyl-2-[[(benzyloxycarbonyl)amino]pentyl]-pyrrolidine;
(3R)-[[N$^\alpha$-(4-biphenylcarbonyl)-L-leucinyl]amino]-1-[(2S)-4-methyl-2-[[(benzyloxycarbonyl)amino]pentyl]-pyrrolidine;
(3R)-[[N-(5-methoxybenzofuran-2-carbonyl)-L-leucinyl]amino]-1-[(2S)-4-methyl-2-[[(benzyloxycarbonyl)amino]pentyl]-pyrrolidine;
(3R)-[[N$^\alpha$-(5-chlorobenzofuran-2-carbonyl)-L-leucinyl]amino]-1-[(2S)-4-methyl-2-[[(benzyloxycarbonyl)amino]pentyl]-pyrrolidine;
(3R)-[[N$^\alpha$-(7-methoxybenzofuran-2-carbonyl)-L-leucinyl]amino]-1-[(2S)-4-methyl-2-[[(benzyloxycarbonyl)amino]pentyl]-pyrrolidine;
(3R)-[[N$^\alpha$-(3-chlorobenzo[b]thiophene-2-carbonyl)-L-leucinyl]amino]-1-[(2S)-4-methyl-2-[[(benzyloxycarbonyl)amino]pentyl]-pyrrolidine;
(3R)-[[N$^\alpha$-(3-(2-pyridyl)benzoyl)-L-leucinyl]amino]-1-[(2S)-4-methyl-2-[[(benzyloxycarbonyl)amino]pentyl]-pyrrolidine;
(3S)-[[N$^\alpha$-(benzo[b]thiophene-2-carbonyl)-L-leucinyl]amino]-1-[(2S)-4-methyl-2-[[(benzyloxycarbonyl)amino]pentyl]-pyrrolidine;
(3S)-[[N$^\alpha$-(3,4-dimethoxybenzoyl)-L-leucinyl]amino]-1-[(2S)-4-methyl-2-[[(benzyloxycarbonyl)amino]pentyl]-pyrrolidine;
(3S)-[[N$^\alpha$-(benzofuran-2-carbonyl)-L-leucinyl]amino]-1-[(2S)-4-methyl-2-[[(benzyloxycarbonyl)amino]pentyl]-pyrrolidine;
(3S)-[[N$^\alpha$-(benzothiazole-6-carbonyl)-L-leucinyl]amino]-1-[(2S)-4-methyl-2-[[(benzyloxycarbonyl)amino]pentyl]-pyrrolidine;
(3S)-[[N$^\alpha$-(indole-2-carbonyl)-L-leucinyl]amino]-1-[(2S)-4-methyl-2-[[(benzyloxycarbonyl)amino]pentyl]-pyrrolidine;
(3S)-[[N$^\alpha$-(4-fluorobenzoyl)-L-leucinyl]amino]-1-[(2S)-4-methyl-2-[[(benzyloxycarbonyl)amino]pentyl]-pyrrolidine;
(3S)-[[N$^\alpha$-(4-methoxybenzoyl)-L-leucinyl]amino]-1-[(2S)-4-methyl-2-[[(benzyloxycarbonyl)amino]pentyl]-pyrrolidine;
(3S)-[[N$^\alpha$-(3,4-dichlorobenzoyl)-L-leucinyl]amino]-1-[(2S)-4-methyl-2-[[(benzyloxycarbonyl)amino]pentyl]-pyrrolidine;
(3S)-[[N$^\alpha$-(thiophene-2-carbonyl)-L-leucinyl]amino]-1-[(2S)-4-methyl-2-[[(benzyloxycarbonyl)amino]pentyl]-pyrrolidine;
(3S)-[[N$^\alpha$-(4-biphenylcarbonyl)-L-leucinyl]amino]-1-[(2S)-4-methyl-2-[[(benzyloxycarbonyl)amino]pentyl]-pyrrolidine;
(3S)-[[N$^\alpha$-(5-methoxybenzofuran-2-carbonyl)-L-leucinyl]amino]-1-[(2S)-4-methyl-2-[[(benzyloxycarbonyl)amino]pentyl]-pyrrolidine;
(3S)-[[N$^\alpha$-(5-chlorobenzofuran-2-carbonyl)-L-leucinyl]amino]-1-[(2S)-4-methyl-2-[[(benzyloxycarbonyl)amino]pentyl]-pyrrolidine;
(3S)-[[N$^\alpha$-(7-methoxybenzofuran-2-carbonyl)-L-leucinyl]amino]-1-[(2S)-4-methyl-2-[[(benzyloxycarbonyl)amino]pentyl]-pyrrolidine;
(3S)-[[N$^\alpha$-(3-chlorobenzo[b]thiophene-2-carbonyl)-L-leucinyl]amino]-1-[(2S)-4-methyl-2-[[(benzyloxycarbonyl)amino]pentyl]-pyrrolidine;
(3S)-[[N$^\alpha$-(3-(2-pyridyl)benzoyl)-L-leucinyl]amino]-1-[(2S)-4-methyl-2-[[(benzyloxycarbonyl)amino]pentyl]-pyrrolidine;
1-(4-phenyl)benzyl-(3S)-[[N$^\alpha$-(tert-butoxycarbonyl)-L-leucinyl]amino]-pyrrolidine;
1-(4-phenyl)benzyl-(3S)-[[N$^\alpha$-(2-naphthylcarbonyl)-L-leucinyl]amino]-pyrrolidine;
1-(4-phenyl)benzyl-(3S)-[[N$^\alpha$-(2-quinolinecarbonyl)-L-leucinyl]amino]-pyrrolidine;
1-(4-phenyl)benzyl-(3S)-[[N$^\alpha$-(3,4-dimethoxybenzoyl)-L-leucinyl]amino]-pyrrolidine;
1-(4-phenyl)benzyl-(3S)-[[N$^\alpha$-(benzofuran-2-carbonyl)-L-leucinyl]amino]-pyrrolidine;
1-(4-phenyl)benzyl-(3S)-[[N$^\alpha$-(benzo[b]thiophene-2-carbonyl)-L-leucinyl]amino]-pyrrolidine;
1-(4-phenyl)benzyl-(3S)-[[N$^\alpha$-(benzyloxycarbonyl)-L-leucinyl]amino]-pyrrolidine,
1-(2-phenyl)ethyl-(3S)-[[N$^\alpha$-(tert-butoxycarbonyl)-L-leucinyl]amino]-pyrrolidine;
1-(2-phenyl)ethyl-(3S)-[[N$^\alpha$-(2-naphthylcarbonyl)-L-leucinyl]amino]-pyrrolidine;
1-(2-phenyl)ethyl-(3S)-[[N$^\alpha$-(2-quinolinecarbonyl)-L-leucinyl]amino]-pyrrolidine;
1-(2-phenyl)ethyl-(3S)-[[N$^\alpha$-(benzo[b]thiophene-2-carbonyl)-L-leucinyl]amino]-pyrrolidine;
1-(2-phenyl)ethyl-(3S)-[[N$^\alpha$-(benzofuran-2-carbonyl)-L-leucinyl]amino]-pyrrolidine;
1-(2-phenyl)ethyl-(3S)-[[N$^\alpha$-(3-chlorobenzo[b]thiophene-2-carbonyl)-L-leucinyl]amino]-pyrrolidine;
1-(4-phenoxy)benzyl-(3S)-[[N$^\alpha$-(tert-butoxycarbonyl)-L-leucinyl]amino]-pyrrolidine;
1-(4-phenoxy)benzyl-(3S)-[[N$^\alpha$-(2-naphthylcarbonyl)-L-leucinyl]amino]-pyrrolidine;
1-(4-phenoxy)benzyl-(3S)-[[N$^\alpha$-(2-quinolinecarbonyl)-L-leucinyl]amino]-pyrrolidine;
1-(4-phenoxy)benzyl-(3S)-[[N$^\alpha$-(3,4-dimethoxybenzoyl)-L-leucinyl]amino]-pyrrolidine;
1-(4-phenoxy)benzyl-(3S)-[[N$^\alpha$-(benzofuran-2-carbonyl)-L-leucinyl]amino]-pyrrolidine
1-(4-phenoxy)benzyl-(3S)-[[N$^\alpha$-(benzo[b]thiophene-2-carbonyl)-L-leucinyl]amino]-pyrrolidine;
1-(4-fluoro)benzyl-(3S)-[[N$^\alpha$-(tert-butoxycarbonyl)-L-leucinyl]amino]-pyrrolidine;
1-(4-fluoro)benzyl-(3S)-[[N$^\alpha$-(2-naphthylcarbonyl)-L-leucinyl]amino]-pyrrolidine;
1-(4-fluoro)benzyl-(3S)-[[N$^\alpha$-(benzo[b]thiophene-2-carbonyl)-L-leucinyl]amino]-pyrrolidine;
1-(4-cyano)benzyl-(3S)-[[N$^\alpha$-(tert-butoxycarbonyl)-L-leucinyl]amino]-pyrrolidine;
1-(4-cyano)benzyl-(3S)-[[N$^\alpha$-(2-naphthylcarbonyl)-L-leucinyl]amino]-pyrrolidine;
1-benzyl-(3S)-[[N$^\alpha$-(benzo[b]thiophene-2-carbonyl)-L-leucinyl]amino]-pyrrolidine;

1-benzyl-(3S)-[[N$^\alpha$-(3,4-dimethoxybenzoyl)-L-leucinyl]amino-pyrrolidine;
1-benzyl-(3S)-[[N$^\alpha$-(3-(2-dimethylaminoethoxy)-4-methoxybenzoyl)-L-leucinyl]amino]-pyrrolidine;
1-(4-nitro)benzyl-(3S)-[[N$^\alpha$-(2-naphthylcarbonyl)-L-leucinyl]amino]-pyrrolidine;
1-(4-(N,N-dimethylamino)benzyl-(3S)-[[N$^\alpha$-(2-naphthylcarbonyl)-L-leucinyl]amino]-pyrrolidine;
1-(4-methoxy)benzyl-(3S)-[[N$^\alpha$-(2-naphthylcarbonyl)-L-leucinyl]amino]-pyrrolidine;
1-(4-pyridyl)methyl-(3S)-[[N$^\alpha$-(2-naphthylcarbonyl)-L-leucinyl]amino]-pyrrolidine;
1]-(4-carboxymethyl)benzyl-(3S)-[[N$^\alpha$-(2-naphthylcarbonyl)-L-leucinyl]amino]-pyrrolidine;
1-(3,4-methylenedioxy)benzyl-(3S)-[[N$^\alpha$-(2-naphthylcarbonyl)-L-leucinyl]amino]-pyrrolidine;
1-(2-naphthyl)methyl-(3S)-[[N$^\alpha$-(2-naphthylcarbonyl)-L-leucinyl]amino]-pyrrolidine;
1-(3-indolyl)methyl-(3S)-[[N$^\alpha$-(2-naphthylcarbonyl)-L-leucinyl]amino]-pyrrolidine;
1-(2-quinolinyl)methyl-(3S)-[[N$^\alpha$-(2-naphthylcarbonyl)-L-leucinyl]amino]-pyrrolidine;
1-(3-quinolinyl)methyl-(3S)-[[N$^\alpha$-(2-naphthylcarbonyl)-L-leucinyl]amino]-pyrrolidine;
1-(1-naphthyl)methyl-(3S)-[[N$^\alpha$-(2-naphthylcarbonyl)-L-leucinyl]amino]-pyrrolidine;
1-(4-quinolinyl)methyl-(3S)-[[N$^\alpha$-(2-naphthylcarbonyl)-L-leucinyl]amino]-pyrrolidine;
1-(3-pyrrolyl)methyl-(3S)-[[N$^\alpha$-(2-naphthylcarbonyl)-L-leucinyl]amino]-pyrrolidine;
1-(3-pyridyl)methyl-(3S)-[[N$^\alpha$-(2-naphthylcarbonyl)-L-leucinyl]amino]-pyrrolidine;
1-(2-pyridyl)methyl-(3S)-[[N$^\alpha$-(2-naphthylcarbonyl)-L-leucinyl]amino]-pyrrolidine;
1-(3-nitro)benzyl-(3S)-[[N$^\alpha$-(2-naphthylcarbonyl)-L-leucinyl]amino]-pyrrolidine;
1-(4-acetamido)benzyl-(3S)-[[N$^\alpha$-(2-naphthylcarbonyl)-L-leucinyl]amino]-pyrrolidine;
1-(3-cyano)benzyl-(3S)-[[N$^\alpha$-(2-naphthylcarbonyl)-L-leucinyl]amino]-pyrrolidine;
1-(3-fluoro)benzyl-(3S)-[[N$^\alpha$-(2-naphthylcarbonyl)-L-leucinyl]amino]-pyrrolidine;
1-(3-phenoxy)benzyl-(3S)-[[N$^\alpha$-(2-naphthylcarbonyl)-L-leucinyl]amino]-pyrrolidine;
1-(4-chloro)benzyl-(3S)-[[N$^\alpha$-(2-naphthylcarbonyl)-L-leucinyl]amino]-pyrrolidine;
1-(4-trifluoromethyl)benzyl-(3S)-[[N$^\alpha$-(2-naphthylcarbonyl)-L-leucinyl]amino]-pyrrolidine;
1-(3-trifluoromethyl)benzyl-(3S)-[[N$^\alpha$-(2-naphthylcarbonyl)-L-leucinyl]amino]-pyrrolidine;
1-(4-(3-(N,N-dimethylamino)propoxy)benzyl-(3S)-[[N$^\alpha$-(2-naphthylcarbonyl)-L-leucinyl]amino]-pyrrolidine;
1-(4-isopropyl)benzyl-(3S)-[[N$^\alpha$-(2-naphthylcarbonyl)-L-leucinyl]amino]-pyrrolidine;
1-(2-benzofuranyl)methyl-(3S)-[[N$^\alpha$-(2-naphthylcarbonyl)-L-leucinyl]amino]-pyrrolidine;
1-(2-(3-methylbenzo[b]thiophenyl)methyl-(3S)-[[N$^\alpha$-(2-naphthylcarbonyl)-L-leucinyl]amino]-pyrrolidine;
1-(2-furanyl)methyl-(3S)-[[N$^\alpha$-(2-naphthylcarbonyl)-L-leucinyl]amino]-pyrrolidine;
1-(3-furanyl)methyl-(3S)-[[N$^\alpha$-(2-naphthylcarbonyl)-L-leucinyl]amino]-pyrrolidine;
1-(2-thiophenyl)methyl-(3S)-[[N$^\alpha$-(2-naphthylcarbonyl)-L-leucinyl]amino]-pyrrolidine;
1-(2-nitro)benzyl-(3S)-[[N$^\alpha$-(2-naphthylcarbonyl)-L-leucinyl]amino]-pyrrolidine;
-(3-thiophenyl)methyl-(3S)-[[N$^\alpha$-(2-naphthylcarbonyl)-L-leucinyl]amino]-pyrrolidine;
1-(3,4-dimethoxy)benzyl-(3S)-[[N$^\alpha$-(2-naphthylcarbonyl)-L-leucinyl]amino]-pyrrolidine; and
1-(5-nitro-3-furanyl)methyl-(3S)-[[N$^\alpha$-(2-naphthylcarbonyl)-L-leucinyl]amino]-pyrrolidine;

or a pharmaceutically acceptable salt thereof.

In yet another aspect, this invention provides novel intermediates useful in the preparation of formula (I) compounds represented by the formula (II):

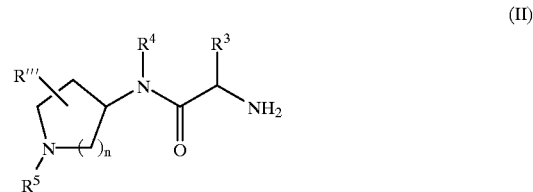

(II)

wherein:

R$^3$ is H, C$_{2-6}$alkenyl, C$_{2-6}$alkynyl, Het, Ar or C$_{1-6}$alkyl optionally substituted by OR', SR', NR'$_2$, N(R')C(O)OR'', CO$_2$R', CO$_2$NR'$_2$, N(C=NH)NH$_2$, Het or Ar;

R$^4$ is H, C$_{1-6}$alkyl, C$_{2-6}$alkenyl, Ar-C$_{0-6}$alkyl, or Het-C$_{0-6}$alkyl;

R$^5$ is

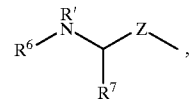

Ar-C$_{0-6}$alkyl, Het-C$_{0-6}$alkyl, adamantyl-C(O)—, Ar-C(O)—, or Het-C(O)—;

R$^6$ is R'', R''C(O), R''C(S), R''SO$_2$, R''OC(O), R''R'NC(O), R''R'NC(S),or R''OC(O)NR'CH(R*)C(O);

R$^7$ is C$_{3-6}$cycloalkyl-C$_{0-6}$alkyl, Ar-C$_{0-6}$alkyl, Het-C$_{0-6}$alkyl, Ar-C$_{0-6}$alkoxy, Het-C$_{0-6}$alkoxy, or C$_{1-6}$alkyl optionally substituted by OR', SR', NR'$_2$, N(R')C(O)OR'', CO$_2$R', CO$_2$NR'$_2$, N(C=NH)NH$_2$, Het or Ar;

R* is H, C$_{1-6}$alkyl, C$_{2-6}$alkenyl, C$_{3-6}$cycloalkyl-C$_{0-6}$-alkyl, Ar-C$_{0-6}$alkyl, Het-C$_{0-6}$alkyl;

each R' independently is H, C$_{1-6}$alkyl, C$_{2-6}$alkenyl, Ar-C$_{0-6}$alkyl, or Het-C$_{0-6}$alkyl;

each R'' independently is C$_{1-6}$alkyl, C$_{3-6}$cycloalkyl-C$_{0-6}$-alkyl, Ar-C$_{0-6}$alkyl, or Het-C$_{0-6}$alkyl;

R''' is H, C$_{1-6}$alkyl, C$_{3-6}$cycloalkyl-C$_{0-6}$alkyl, Ar-C$_{0-6}$alkyl, or Het-C$_{0-6}$alkyl;

Z is C(O) or CH$_2$; and n is 1, 2 or 3;

or a pharmaceutically acceptable salt thereof.

Abbreviations and symbols commonly used in the peptide and chemical arts are used herein to describe the compounds of the present invention. In general, the amino acid abbreviations follow the IUPAC-IUB Joint Commission on Biochemical Nomenclature as described in *Eur. J. Biochem.*, 158, 9 (1984). The term "amino acid" as used herein refers to the D- or L-isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

"C$_{1-6}$alkyl" as applied herein is meant to include substituted and unsubstituted methyl, ethyl, n-propyl, isopropyl, n-butyl, isobutyl and t-butyl, pentyl, n-pentyl, isopentyl, neopentyl and hexyl and the simple aliphatic isomers thereof. Any $C_{1-6}$alkyl group may be optionally substituted independently by one or two halogens, SR', OR', N(R')$_2$, C(O)N(R')$_2$, carbamyl or $C_{1-4}$alkyl, where R' is H or $C_{1-6}$alkyl. $C_0$alkyl means that no alkyl group is present in the moiety. Thus, Ar-$C_0$alkyl is equivalent to Ar.

"$C_{3-6}$cycloalkyl" as applied herein is meant to include substituted and unsubstituted cyclopropane, cyclobutane, cyclopentane, and cyclohexane.

"$C_{2-6}$ alkenyl" as applied herein means an alkyl group of 2 to 6 carbons wherein a carbon-carbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included.

"$C_{2-6}$alkynyl" means an alkyl group of 2 to 6 carbons wherein one carbon-carbon single bond is replaced by a carbon-carbon triple bond. $C_{2-6}$ alkynyl includes acetylene, 1-propyne, 2-propyne, 1-butyne, 2-butyne, 3-butyne and the simple isomers of pentyne and hexyne.

"Halogen" or "halo" means F, Cl, Br, and I.

"Ar" or "aryl" means unsubstituted phenyl or naphthyl; or phenyl or naphthyl substituted by one or more of Ph-$C_{0-6}$alkyl, Het-$C_{0-6}$alkyl, $C_{1-6}$alkoxy, Ph-$C_{0-6}$alkoxy, Het-$C_{0-6}$alkoxy, OH, (CH$_2$)$_{1-6}$NR'R', O(CH$_2$)$_{1-6}$NR'R'; wherein each R' independently is H, $C_{1-6}$alkyl, Ar-$C_{0-6}$alkyl, or Het-$C_{0-6}$alkyl; or phenyl or naphthyl substituted by one to three moieties selected from $C_{1-4}$alkyl, OR', N(R')$_2$, SR', CF$_3$, NO$_2$, CN, CO$_2$R', CON(R'), F, Cl, Br and I, or substituted by a methylenedioxy group.

As used herein "Het" or "heterocyclic" or "heteroaryl" represents a stable 5- to 7-membered monocyclic or a stable 7- to 10-membered bicyclic heterocyclic ring, which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure, and may optionally be substituted with one or two moieties selected from $C_{1-4}$alkyl, OR', N(R')$_2$, SR', CF$_3$, NO$_2$, CN, CO$_2$R', CON(R'), F, Cl, Br and I, where R' is as defined hereinbefore. Examples of such heterocycles include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, pyridyl, pyrazinyl, oxazolidinyl, oxazolinyl, oxazolyl, isoxazolyl, morpholinyl, thiazolidinyl, thiazolinyl, thiazolyl, quinuclidinyl, indolyl, quinolinyl, isoquinolinyl, benzimidazolyl, benzopyranyl, benzoxazolyl, furyl, pyranyl, tetrahydrofuryl, tetrahydropyranyl, thienyl, benzoxazolyl, thiamorpholinyl sulfoxide, thiamorpholinyl sulfone, oxadiazolyl, benzothiazolyl, benzoisothiazolyl, benzisoxazolyl, pyrimidinyl, cinnolinyl, quinazolinyl, quinoxalinyl, 1,5-napthyridinyl, 1,6-napthyridinyl, 1,7-napthyridinyl, 1,8-napthyridinyl, tetrazolyl, 1,2,3-triazolyl, and 1,2,4-triazolyl. "Het" also means any heterocyclic moiety encompassed by the above definition of Het which is aromatic in character, e.g., pyridinyl, quinolinyl, isoquinolinyl, pyrrolyl, pyrazolyl, imidazolyl, pyridyl, pyrazinyl, oxazolyl, isoxazolyl, thiazolyl, isothiazolyl, indolyl, quinolinyl, isoquinolinyl, benzimidazolyl, benzoxazolyl, furyl, thienyl, benzoxazolyl, oxadiazolyl, benzothiazolyl, benzoisothiazolyl, benzisoxazolyl, pyrimidinyl, cinnolinyl, quinazolinyl, quinoxalinyl, 1,5-napthyridinyl, 1,6-napthyridinyl, 1,7-napthyridinyl, 1,8-napthyridinyl, tetrazolyl, 1,2,3-triazolyl, and 1,2,4-triazolyl.

Certain radical groups are abbreviated herein. t-Bu refers to the tertiary butyl radical, Boc or BOC refers to the t-butyloxycarbonyl radical, Fmoc refers to the fluorenylmethoxycarbonyl radical, Ph refers to the phenyl radical, Cbz or CBZ refers to the benzyloxycarbonyl radical.

Certain reagents are abbreviated herein. DCC refers to dicyclohexylcarbodiimide, DMAP is 2,6-dimethylaminopyridine, EDC or EDCI refers to N-ethyl-N' (dimethylaminopropyl)-carbodiimide. HOBT or HOBt refers to 1-hydroxybenzotriazole, DMF refers to dimethyl formamide, BOP refers to benzotriazol-1-yloxy-tris (dimethylamino)phosphonium hexafluorophosphate, DMAP is dimethylaminopyridine, DIEA refers to di-isopropylethylamine, Lawesson's reagent is 2,4-bis(4-methoxyphenyl)-1,3-dithia-2,4-diphosphetane-2,4-disulfide, NMM is N-methylmorpholine, TFA refers to trifluoroacetic acid, TFAA refers to trifluoroacetic anhydride, KHMDS refers to potassium hexamethyldisilazide, and THF refers to tetrahydrofuran. Jones reagent is a solution of chromium trioxide, water, and sulfuric acid well-known in the art.

Compounds of the formula (I) are generally prepared by reacting a compound of the formula (II):

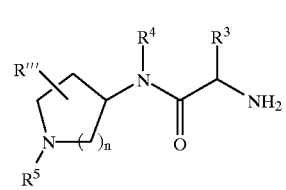

(II)

or a salt thereof, wherein R''', R$^3$, R$^4$, R$^5$ and n are as defined in formula (I), with any reactive functional groups protected, with:
(a) R"C(O)Cl, in which R" is as defined in formula (I) of claim 1; or
(b) R"C(O)OH, in which R" is as defined in formula (I) of claim 1, in the presence of EDC and HOBT; or
(c) R"C(O)H, in which R" is as defined in formula (I) of claim 1, followed by reduction; or
(d) R"OC(O)Cl, in which R" is as defined in formula (I) of claim 1, in the presence of base; or
(e) R"SO$_2$Cl, in which R" is as defined in formula (I) of claim 1, in the presence of base;

and thereafter removing any protecting groups and optionally forming a pharmaceutically acceptable salt.

Compounds of the formula (I) are prepared by methods analogous to those described in Schemes 1 and 2.

Scheme 1

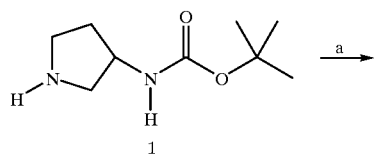

1

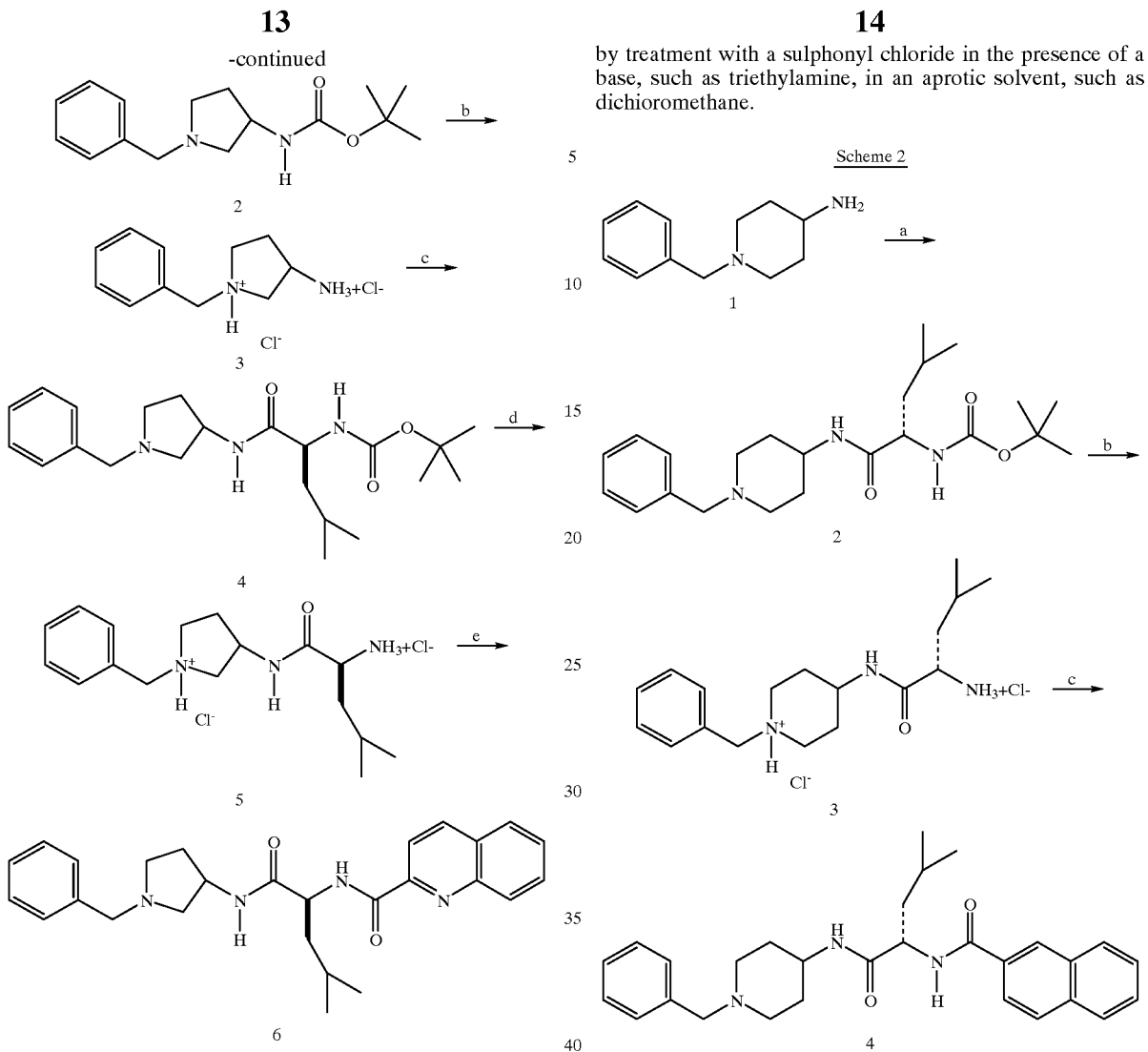

a) PhCHO, CH$_2$Cl$_2$, NaBH(OAc)$_3$; b) HCl, EtOAc, CH$_3$OH; c) N-BOC-leucine, EDC, HOBt, NMM, CH$_2$Cl$_2$; d) HCl, EtOAc, CH$_3$OH; e) quinaldic acid, EDC, HOBt, NMM, CH$_2$Cl$_2$ Compounds of the general formula (1) wherein n is 1, R$^5$ is an alkyl group and R$^1$ is an R'C(O) can be prepared as outlined in Scheme 1. Reductive alkylation of the commercially available amine 1-Scheme-1 (this material available in racemic or enantiomerically pure form) with an aldehyde, such as benzaldehyde or CBZ-leucinal, follwed by treatment with a reducing agent, such as sodium triacetoxyborohydride, affords the tertiary amine 2-Scheme-1. Removal of the protecting group by treating 2-Scheme-1 with a strong acid, such as hydrogen chloride, in ethyl acetate or ether or dioxane and methanol affords 3-Scheme-1. 3-Scheme-1 may be coupled with an acid using EDC and HOBT in the presence of a base, such as N-methylmorpholine or triethylamine, in an aprotic solvent, such as dichloromethane, to yield 4-Scheme-1. The protecting group of 4-Scheme-1 may be removed with strong acid, such as hydrogen chloride, in ethyl acetate or ether or dioxane and methanol to afford 5-Scheme-1. Coupling of the amine salt 5-Scheme-1 may be effected with an acid in the presence of EDC, HOBt and a base, such as N-methylmorpholine, to yield 6-Scheme-1. The 5-Scheme-1 salt may also be converted to the sulphonamide derivative by treatment with a sulphonyl chloride in the presence of a base, such as triethylamine, in an aprotic solvent, such as dichloromethane.

a) N-BOC-leucine, EDC, HOBT, NMM, CH$_2$Cl$_2$; b) HCl, EtOAc; c) 2-naphthoic acid, EDC, HOBT, CH$_2$Cl$_2$, NMM Compounds of the general formula (I) wherein n is 2, R$^5$ is a benzyl group and R$^1$ is an R' C(O) can be prepared as outlined in Scheme 1. Acylation of the commercially available 4-amino-1-benzylpiperidine (1-Scheme-1) with N-BOC-leucine in the presence of EDC, HOBT and N-methylmorpholine in dichloromethane afforded 2-scheme-2. Removal of the protecting group with anhydrous hydrogen chloride in ethyl acetate or ether or dioxane and methanol gave 3-Scheme-2. Acylation of the amine salt 3-Scheme-2 with a carboxylic acid as described previously afforded 4-Scheme-2.

The starting materials used herein are commercially available amino acids or are prepared by routine methods well known to those of ordinary skill in the art and can be found in standard reference books, such as the COMPENDIUM OF ORGANIC SYNTHETIC METHODS, Vol. I–VI (published by Wiley-Interscience).

Coupling methods to form amide bonds herein are generally well known to the art. The methods of peptide synthesis generally set forth by Bodansky et al., THE PRACTICE OF PEPTIDE SYNTHESIS, Springer-Verlag, Berlin, 1984; E. Gross and J. Meienhofer, THE PEPTIDES, Vol. 1, 1–284 (1979); and J. M. Stewart and J. D. Young, SOLID PHASE PEPTIDE SYNTHESIS, 2d Ed., Pierce Chemical Co., Rockford, Ill., 1984. are generally illustrative of the technique and are incorporated herein by reference.

Synthetic methods to prepare the compounds of this invention frequently employ protective groups to mask a reactive functionality or minimize unwanted side reactions. Such protective groups are described generally in Green, T. W, PROTECTIVE GROUPS IN ORGANIC SYNTHESIS, John Wiley & Sons, New York (1981). The term "amino protecting groups" generally refers to the Boc, acetyl, benzoyl, Fmoc and Cbz groups and derivatives thereof as known to the art. Methods for protection and deprotection, and replacement of an amino protecting group with another moiety are well known.

Acid addition salts of the compounds of formula (I) are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts. Halides, sulfate, phosphate, alkanoates (such as acetate and trifluoroacetate), benzoates, and sulfonates (such as mesylate) are examples of anions present in pharmaceutically acceptable salts.

This invention also provides a pharmaceutical composition which comprises a compound according to formula (I) and a pharmaceutically acceptable carrier, diluent or excipient. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds of formula (I) are useful as protease inhibitors, particularly as inhibitors of cysteine and serine proteases, more particularly as inhibitors of cysteine proteases, even more particularly as inhibitors of cysteine proteases of the papain superfamily, yet more particularly as inhibitors of cysteine proteases of the cathepsin family, most particularly as inhibitors of cathepsin K. The present invention also provides useful compositions and formulations of said compounds, including pharmaceutical compositions and formulations of said compounds.

The present compounds are useful for treating diseases in which cysteine proteases are implicated, including infections by pneumocystis carinii, trypsanoma cruzi, trypsanoma brucei, and *Crithidia fusiculata;* as well as in schistosomiasis, malaria, tumor metastasis, metachromatic leukodystrophy, muscular dystrophy, amytrophy; and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease; hypercalcemia of malignancy, and metabolic bone disease.

Metastatic neoplastic cells also typically express high levels of proteolytic enzymes that degrade the surrounding matrix, and certain tumors and metastatic neoplasias may be effectively treated with the compounds of this invention.

The present invention also provides methods of treatment of diseases caused by pathological levels of proteases, particularly cysteine and serine proteases, more particularly cysteine proteases, even more particularly as inhibitors of cysteine proteases of the papain superfamily, yet more particularly cysteine proteases of the cathepsin family, which methods comprise administering to an animal, particularly a mammal, most particularly a human in need thereof a compound of the present invention. The present invention especially provides methods of treatment of diseases caused by pathological levels of cathepsin K, which methods comprise administering to an animal, particularly a mammal, most particularly a human in need thereof an inhibitor of cathepsin K, including a compound of the present invention. The present invention particularly provides methods for treating diseases in which cysteine proteases are implicated, including infections by pneumocystis carinii, trypsanoma cruzi, trypsanoma brucei, and *Crithidia fusiculata;* as well as in schistosomiasis, malaria, tumor metastasis, metachromatic leukodystrophy, muscular dystrophy, amytrophy, and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease, hypercalcemia of malignancy, and metabolic bone disease.

This invention further provides a method for treating osteoporosis or inhibiting bone loss which comprises internal administration to a patient of an effective amount of a compound of formula (I), alone or in combination with other inhibitors of bone resorption, such as bisphosphonates (i.e., allendronate), hormone replacement therapy, anti-estrogens, or calcitonin. In addition, treatment with a compound of this invention and an anabolic agent, such as bone morphogenic protein, iproflavone, may be used to prevent bone loss or to increase bone mass.

For acute therapy, parenteral administration of a compound of formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit cathepsin K. The compounds are administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention.

The compounds of this invention may be tested in one of several biological assays to determine the concentration of compound which is required to have a given pharmacological effect.

Determination of Cathepsin K Proteolytic Catalytic Activity

All assays for cathepsin K were carried out with human recombinant enzyme. Standard assay conditions for the determination of kinetic constants used a fluorogenic peptide substrate, typically Cbz-Phe-Arg-AMC, and were determined in 100 mM Na acetate at pH 5.5 containing 20 mM cysteine and 5 mM EDTA. Stock substrate solutions were prepared at concentrations of 10 or 20 mM in DMSO with 20 uM final substrate concentration in the assays. All assays contained 10% DMSO. Independent experiments found that this level of DMSO had no effect on enzyme activity or kinetic constants. All assays were conducted at ambient temperature. Product fluorescence (excitation at 360 nM; emission at 460 nM) was monitored with a Perceptive Biosystems Cytofluor II fluorescent plate reader. Product progress curves were generated over 20 to 30 minutes following formation of AMC product.

Inhibition Studies

Potential inhibitors were evaluated using the progress curve method. Assays were carried out in the presence of variable concentrations of test compound. Reactions were initiated by addition of enzyme to buffered solutions of inhibitor and substrate. Data analysis was conducted according to one of two procedures depending on the appearance of the progress curves in the presence of inhibitors. For those compounds whose progress curves were linear, apparent inhibition constants ($K_{i,app}$) were calculated according to equation 1 (Brandt et al., *Biochemitsry*, 1989, 28, 140):

$$v 32 V_m A/[K_a(1+I/K_{i,\ app})+A] \qquad (1)$$

where v is the velocity of the reaction with maximal velocity $V_m$, A is the concentration of substrate with Michaelis constant of $K_a$, and I is the concentration of inhibitor.

For those compounds whose progress curves showed downward curvature characteristic of time-dependent inhibition, the data from individual sets was analyzed to give $k_{obs}$ according to equation 2:

$$[AMC]=v_{ss}t+(v_0-v_{ss})[1-\exp(-k_{obs}t)]/k_{obs} \qquad (2)$$

where [AMC] is the concentration of product formed over time t, $v_0$ is the initial reaction velocity and $v_{ss}$ is the final steady state rate. Values for $k_{obs}$ were then analyzed as a linear function of inhibitor concentration to generate an apparent second order rate constant ($k_{obs}$/inhibitor concentration or $k_{obs}/[I]$) describing the time-dependent inhibition. A complete discussion of this kinetic treatment has been fully described (Morrison et al., *Adv. Enzymol. Relat. Areas Mol. Biol.*, 1988, 61, 201).

One skilled in the art would consider any compound with a $K_i$ of less than 50 micromolar to be a potential lead compound. Preferably, the compounds used in the method of the present invention have a $K_i$ value of less than 1 micromolar. Most preferably, said compounds have a $K_i$ value of less than 100 nanomolar. 4-(R,S)-Amino-N-[(8-quinolinesulfonyl)-S-leucine]-3-tetrahydrofuran-3-one, a compound of formula (I), has a $K_i$ value that is greater than 10 micromolar.

Human Osteoclast Resorption Assay

Aliquots of osteoclastoma-derived cell suspensions were removed from liquid nitrogen storage, warmed rapidly at 37° C. and washed ×1 in RPMI-1640 medium by centrifugation (1000 rpm, 5 min at 4° C.). The medium was aspirated and replaced with murine anti-HLA-DR antibody, diluted 1:3 in RPMI-1640 medium, and incubated for 30 min on ice The cell suspension was mixed frequently.

The cells were washed ×2 with cold RPMI-1640 by centrifugation (1000 rpm, 5 min at 4° C.) and then transferred to a sterile 15 mL centrifuge tube. The number of mononuclear cells were enumerated in an improved Neubauer counting chamber.

Sufficient magnetic beads (5/mononuclear cell), coated with goat anti-mouse IgG, were removed from their stock bottle and placed into 5 mL of fresh medium (this washes away the toxic azide preservative). The medium was removed by immobilizing the beads on a magnet and is replaced with fresh medium.

The beads were mixed with the cells and the suspension was incubated for 30 min on ice. The suspension was mixed frequently. The bead-coated cells were immobilized on a magnet and the remaining cells (osteoclast-rich fraction) were decanted into a sterile 50 mL centrifuge tube. Fresh medium was added to the bead-coated cells to dislodge any trapped osteoclasts. This wash process was repeated ×10. The bead-coated cells were discarded.

The osteoclasts were enumerated in a counting chamber, using a large-bore disposable plastic pasteur pipette to charge the chamber with the sample. The cells were pelleted by centrifugation and the density of osteoclasts adjusted to $1.5\times10^4$/mL in EMEM medium, supplemented with 10% fetal calf serum and 1.7 g/liter of sodium bicarbonate. 3 mL aliquots of the cell suspension (per treatment) were decanted into 15 mL centrifuge tubes. These cells were pelleted by centrifugation. To each tube 3 mL of the appropriate treatment was added (diluted to 50 uM in the EMEM medium). Also included were appropriate vehicle controls, a positive control (87MEM1 diluted to 100 ug/mL) and an isotype control (IgG2a diluted to 100 ug/mL). The tubes were incubate at 37° C. for 30 min.

0.5 mL aliquots of the cells were seeded onto sterile dentine slices in a 48-well plate and incubated at 37° C. for 2 h. Each treatment was screened in quadruplicate. The slices were washed in six changes of warm PBS (10 mL/well in a 6-well plate) and then placed into fresh treatment or control and incubated at 37° C. for 48 h. The slices were then washed in phosphate buffered saline and fixed in 2% glutaraldehyde (in 0.2M sodium cacodylate) for 5 min., following which they were washed in water and incubated in buffer for 5 min at 37° C. The slices were then washed in cold water and incubated in cold acetate buffer/fast red garnet for 5 min at 4° C. Excess buffer was aspirated, and the slices were air dried following a wash in water.

The TRAP positive osteoclasts were enumerated by bright-field microscopy and were then removed from the surface of the dentine by sonication. Pit volumes were determined using the Nikon/Lasertec ILM21W confocal microscope.

EXAMPLES

Nuclear magnetic resonance spectra were recorded at either 250 or 400 MHz using, respectively, a Bruker AM 250 or Bruker AC 400 spectrometer. $CDCl_3$ is deuteriochloroform, $DMSO-d_6$ is hexadeuteriodimethylsulfoxide, and $CD_3OD$ is tetradeuteriomethanol. Chemical shifts are reported in parts per million (d) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Centigrade (° C.).

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel.

Where indicated, certain of the materials were purchased from the Aldrich Chemical Co., Milwaukee, Wis., Chemical Dynamics Corp., South Plainfield, N.J., and Advanced Chemtech, Louisville, Ky.

Unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

Example 1

Preparation of 3-[[N$^\alpha$-(2-quinolinecarbonyl)-L-leucinyl]amino]-1-[(2S)-4-methyl-2-[[(benzyloxycarbonyl)amino]pentyl]-pyrrolidine a.) 3-[(tert-butoxycarbonyl)amino]-1-[(2S)-4-methyl-2-[[(benzyloxycarbonyl)amino]pentyl]-pyrrolidine To a solution of 3-(tert-butoxycarbonylamino)pyrrolidine (2.0 g, 10.74 mmol) in $CH_2Cl_2$ was added CBZ-leucinal (3.2 g, 12.88 mmol). The reaction was allowed to stir at room temperature for approximately 1 hour whereupon sodium triacetoxyborohydride (3.4 g, 16.11 mmol) was added in a single portion. The reaction was stirred an additional 2 hours whereupon it was diluted with ethyl acetate and washed with sat'd NaHCO3, brine, dried ($Na_2SO_4$), concentrated and chromatographed (5% $CH_3OH:CH_2Cl_2$) to give 4.3 g of the title compound: MS(ES+) 420 (MH$^+$).

b.) 3-amino-1-[(2S)-4-methyl-2-[[(benzyloxycarbonyl)amino]pentyl]-pyrrolidine bis hydrochloride To a solution of the compound of Example 1(a) (4.3 g) in $CH_3OH$ (10 mL) was added 4M HCl in dioxane (10 mL). The reaction was stirred at room temperature for 4 hours whereupon it was concentrated in vacuo to yield 3.97 g of the title compound: MS(ES+) 320 (MH$^+$).

c.) 3-[[N$^\alpha$-(tert-butoxycarbonyl)-L-leucinyl]amino]-1-[(2S)-4-methyl-2-[[(benzyloxycarbonyl)amino] pentyl]-pyrrolidine To a solution of the compound of Example 1(b) (2.0 g, 5.1 mmole) was added EDC (1.27 g, 6.37 mmol) HOBT (724 mg, 5.35 mmol) TEA (1.78 mL, 12.75 mmol) and N-BOC-leucine (1.3 g, 5.35 mmol) The reaction was stirred until complete as indicated by TLC analysis whereupon it was diluted with ethyl acetate and washed with 5% NaHCO$_3$, brine, dried (MgSO$_4$), filtered, concentrated and chromatographed (5% $CH_3OH:CH_2Cl_2$) to give 2.7 g of the title compound: MS(ES+) 533 (MH$^+$)

d.) 3-L-leucinyl-1-[(2S)-4-methyl-2-[[(benzyloxycarbonyl)amino]pentyl]-pyrrolidine bis hydrochloride Following the procedure of Example 1(b) except substituting the compound of Example 1(c), the title compound was produced: MS(ES+) 433 (MH$^+$).

e.) 3-[[N$^\alpha$-(2-quinolinecarbonyl)-L-leucinyl]amino]-1-[(2S)-4-methyl-2-[[(benzyloxycarbonyl)amino] pentyl]-pyrrolidine Following the procedure of Example 1(c) except substituting the compound of Example 1(d) and quinaldic acid for N-BOC-leucine, the title compound was produced: MS(ES+) 588 (MH$^+$).

Example 2

Preparation of 1-benzyl-3-[[N$^\alpha$-(2-quinolinecarbonyl)-L-leucinyl]amino]-pyrrolidine a.) 1-benzyl-3-[[N$^\alpha$-(tert-butoxycarbonyl)-L-leucinyl]amino]-pyrrolidine Following the procedure of Example 1(c) except substituting 1-benzyl-3-aminopyrrolidine, the title compound was prepared. MS(ES+) 390 (MH$^+$).

b.) 1-benzyl-3-L-leucinyl-pyrrolidine bis hydrochloride

Following the procedure of Example 1(b) except substituting the compound of Example 2(a), the title compound was prepared: MS(ES+) 290 (MH$^+$).

c.) 1-benzyl-3-[[N$^\alpha$-(2-quinolinecarbonyl)-L-leucinyl]amino]-pyrrolidine

Following the procedure of Example 1(e) except substituting the compound of Example 2(b), the title compound was prepared: MS(ES+) 445 (MH$^+$).

Example 3

Preparation of 3-[[N$^\alpha$-(2-naphthylcarbonyl)-L-leucinyl]amino]-1-[(2S)-4-methyl-2-[[(benzyloxycarbonyl)amino]pentyl]-pyrrolidine Following the procedure of Example 1(e) except substituting 2-naphthoic acid for quinaldic acid, the title compound was prepared: MS(ES+) 587 (MH+).

Example 4

Preparation of 1-benzyl-3-[[N$^\alpha$-(2-naphthylcarbonyl)-L-leucinyl]amino]-pyrrolidine Following the procedure of Example 2(c) except substituting 2-naphthoic acid for quinaldic acid, the title compound was produced: MS(ES+) 444 (MH$^+$).

Example 5

Preparation of 1-benzyl-((3S))-[[N$^\alpha$-(benzyloxycabonyl)-L-leucinyl]amino]-pyrrolidine a.) 1-benzyl-((3S))-(tert-butoxycarbonyl)amino-pyrrolidine Following the procedure of Example 1(a) except substituting ((3S))-(−)-3-(tert-butoxycarbonylamino)pyrrolidine for 3-(tert-butoxycarbonylamino)pyrrolidine and benzaldehyde for CBZ-leucinal, the title compound was prepared: MS(ES+) 221.2 (M-C$_4$H$_8$), 277.3 (MH$^+$).

b.) 1-benzyl-((3S))-amino-pyrrolidine bis hydrochloride

To a solution of the compound of Example 5(a) in methanol was added a 1M HCl/ether. The reaction was stirred at room temperature until complete as indicated by mass spectral analysis. The reaction was concentrated in vacuo to give a white solid: MS(ES+) 177.0 (MH$^+$).

c.) 1-benzyl-((3S))-[[N$^\alpha$-(benzyloxycarbonyl)-L-leucinyl]amino]-pyrrolidine Following the procedure of Example 1(c) except substituting the compound of Example 5(b) and CBZ-leucine for BOC-leucine, the title compound was prepared: MS(ES+) 424.2(MH$^+$).

Example 6

Preparation of 1-benzyl-((3S))-[[N$^\alpha$-(tert-butoxycarbonyl)-L-leucinyl]amino]-pyrrolidine Following the procedure of Example 5(c) except substituting BOC-leucine for CBZ-leucine, the title compound was prepared: MS(ES+) 390.5 (MH$^+$).

Example 7

Preparation of ((3S))-[[N$^\alpha$-(2-naphthylcarbonyl)-L-leucinyl]amino]-1-[(2S)-4-methyl-2-[[(benzyloxycarbonyl)amino]pentyl]-pyrrolidine a.) ((3S))-[(tert-butoxycarbonyl)amino]-1-[(2S)-4-methyl-2-[[(benzyloxycarbonyl)amino]pentyl]-pyrrolidine Following the procedure of Example 1(a) except substituting ((3S))-(−)-3-(tert-butoxycarbonylamino)pyrrolidine for 3-(tert-butoxycarbonylamino)pyrrolidine the title compound was prepared: MS(ES+) 420 (MH$^+$).

b.) ((3S))-[(tert-butoxycarbonyl)amino]-1-[(2S)-4-methyl-2-[[(benzyloxycarbonyl)amino]pentyl]-pyrrolidine Following the procedure of Example 1(b) except substituting the compound of Example 7(a), the title compound was produced: MS(ES) 320 (MH$^+$)

c.) (3S)-[[N$^\alpha$-(tert-butoxycarbonyl)-L-leucinyl]amino]-1-[(2S)-4-methyl-2-[[(benzyloxycarbonyl)amino]pentyl]-pyrrolidine Following the procedure of Example 1(c) except substituting the compound of Example 7(b), the title compound was produced: MS(ES+) 533 (MH$^+$).

d.) (3S)-L-leucinyl-1-[(2S)-4-methyl-2-[[(benzyloxycarbonyl)amino]pentyl]-pyrrolidine bis hydrochloride Following the procedure of Example 1(d) except substituting the compound of Example 7(c), the title compound was prepared: MS(ES+) 433 (MH$^+$).

e.) (3S)-[[N$^\alpha$-(2-naphythylcarbonyl)-L-leucinyl]amino]-1-[(2S)-4-methyl-2-[[(benzyloxycarbonyl)amino]pentyl]-pyrrolidine Following the procedure of Example 1(e) except substituting the compound of Example7(d) and substituting 2-naphthoic acid for quinaldic acid, the title compound was produced: MS(ES+) 587 (MH$^+$).

Example 8

Preparation of (3R)-[[N$^\alpha$-(2-naphthylcarbonyl)-L-leucinyl]amino]-1-[(2S)-4-methyl-2-[[(benzyloxycarbonyl)amino]pentyl]-pyrrolidine a.) (3R)-[(tert-butoxycarbonyl)amino]-1-[(2S)-4-methyl-2-[[(benzyloxycarbonyl)amino]pentyl]-pyrrolidine Following the procedure of Example 1(a) except substituting (3R)-(−)-3-(tert-butoxycarbonylamino)pyrrolidine for 3-(tert-butoxycarbonylamino)pyrrolidine the title compound was prepared: MS(ES+) 420 (MH$^+$).

b.) (3R)-amino-1-[(2S)-4-methyl-2-[[(benzyloxycarbonyl)amino]pentyl]-pyrrolidine Following the procedure of Example 1(b) except substituting the compound of Example 8(a), the title compound was produced: 320 MS(ES) (MH$^+$)

c.) (3R)-[[N$^\alpha$-(tert-butoxycarbonyl)-L-leucinyl]amino]-1-[(2S)-4-methyl-2-[[(benzyloxycarbonyl)amino]pentyl]-pyrrolidine Following the procedure of Example 1(c) except substituting the compound of Example 8(b), the title compound was produced: 533 MS(ES+) (MH$^+$).

d.) (3R)-L-leucinyl-1-[(2S)-4-methyl-2-[[(benzyloxycarbonyl)amino]pentyl]-pyrrolidine bis hydrochloride Following the procedure of Example 1(d) except substituting the compound of Example 8(c), the title compound was prepared: MS(ES+) 433 (MH$^+$).

e.) (3R)-[[N$^\alpha$-(2-naphthylcarbonyl)-L-leucinyl]amino]-1-[(2S)-4-methyl-2-[[(benzyloxycarbonyl)amino]pentyl]-pyrrolidine Following the procedure of Example 1(e) except substituting the compound of Example 8(d) and substituting 2-naphthoic acid for quinaldic acid, the title compound was produced: MS(ES+) 587 (MH+).

Example 9

Preparation of 1-benzyl-(3R)-[[N$^\alpha$-(2-quinolineacetonoyi)-L-leucinyl]amino]-pyrrolidine a.) 1-benzyl-(3R)-[(tert-butoxycarbonyl)amino]-pyrrolidine To a solution of ((3R))-(−)-3-(tert-butoxycarbonylamino) pyrrolidine (2.0 g, 10.73 mmol) in $CH_2Cl_2$ (20 mL) was added benzaldehyde (1.3 mL, 12.88 mmol). The reaction was stirred at room temperature for 2 hours whereupon sodium triacetoxyborohydride (5.68 g, 26.82 mmol) was added. The reaction was stirred overnight at room temperature whereupon it was diluted with ethyl acetate and washed with sat. $K_2CO_3$, water, brine, dried ($MgSO_4$), filtered, concentrated and chromatographed (1:1 hex:EtOAc) to give the title compound: MS(ES+) 221.1 (M-$C_4H_8$), 277.2 (MH+)

b.) 1-benzyl-(3R)-amino-pyrrolidine bis hydrochloride

To a solution of the compound of Example 9(a) in methanol was added 1N HCl/ether. The suspension was stirred at room temperature until complete as indicated by mass spectral analysis. The reaction was concentrated in vacuo to give the title compound: MS(ES+) 176.9 (MH+).

c). 1-benzyl-(3R)-[[N$^\alpha$-(tert-butoxycarbonyl)-L-leucinyl]amino]-pyrrolidine Following the procedure of Example 1(c) except substituting the compound of Example 9(b) and N-methylmorpholine for triethylamine, the title compound was produced: MS(ES+) 390.3 (MH+).

d.) 1-benzyl-(3R)-[(L-leucinyl]amino]-pyrrolidine bis hydrochloride

To a solution of the compound of Example 9(c) in ethyl acetate and methanol was bubbled HCl gas for ca. 2 mins. The reaction was stirred overnight whereupon it was concentrated in vacuo to afford the title compound: MS(ES+) 290.4 (MH+).

e.) 1-benzyl-(3R)-[[N$^\alpha$-(2-naphthylacetonoyl)-L-leucinyl]amino]-pyrrolidine To a suspension of the compound of Example 9(d) (75 mg) was added EDC (44.3 mg), HOBT (28.4 mg) NMM (0.14 mL) and 2-naphthylacetic acid. The reaction was stirred overnight at room temperature whereupon it was diluted wiyh ethyl acetae and washed with sat. $K_2CO_3$, water, brine, dried ($MgSO_4$), filtered, concentrated and chromatographed to give the title compound: MS(ES+) 458.3 (MH+).

Example 10

Preparation of 1-benzyl-(3R)-[[N$^\alpha$-(2-naphthylcarbonyl)-L-leucinyl]amino]-pyrrolidine Following the procedure of Example 9(e) except substituting 2-naphthoic acid for 2-naphthylacetic acid, the title compound was prepared: MS(ES+) 444.2 (MH+).

Example 11

Preparation of 1-benzyl-(3R)-[[N$^\alpha$-(3-quinolinecarbonyl)-L-leucinyl]amino]-pyrrolidine Following the procedure of Example 9(e) except substituting 3-quinolinecarboxylic acid for 2-naphthylacetic acid, the title compound was prepared: MS(ES+) 445.3 (MH+).

Example 12

Preparation of 1-benzyl-(3R)-[[N$^\alpha$-(2-quinolinecarbonyl)-L-leucinyl]amino]-pyrrolidine Following the procedure of Example 9(e) except substituting quinaldic acid for 2-naphthylacetic acid, the title compound was prepared: MS(ES+) 445.2 (MH+).

Example 13

Preparation of 1-benzyl-(3R)-[[N$^\alpha$-(3-isoquinolinecarbonyl)-L-leucinyl]amino]-pyrrolidine Following the procedure of Example 9(e) except substituting 3-isoquinolinecarboxylic acid for 2-naphthylacetic acid, the title compound was prepared: MS(ES+) 445.3 (MH+).

Example 14

Preparation of 1-benzyl-(3S)-[[N$^\alpha$-(2-naphthylacetonoyl)-L-leucinyl]amino]-pyrrolidine a.) 1-benzyl-(3S)-[(tert-butoxycarbonyl)amino]-pyrrolidine Following the procedure of Example 9(a) except substituting ((3S))-(−)-3-(tert-butoxycarbonylamino)pyrrolidine for (3R)-(−)-3-(tert-butoxycarbonylamino)pyrrolidine, the title compound was produced: MS(ES+) 277.2 (MH+).

b.) 1-benzyl-(3S)-amino-pyrrolidine bis hydrochloride

Following the procedure of Example 9(b) except substituting the compound of example 14(a), the title compound was produced: MS(ES+) 177.0 (MH+).

c.) 1-benzyl-(3S)-[[N$^\alpha$-(tert-butoxycarbonyl)-L-leucinyl]amino]-pyrrolidine Following the procedure of Example 9(c) except substituting the compound of Example 14(b), the title compound was produced: MS(ES+) 390.3 (MH+).

d.) 1-benzyl-(3S)-[(L-leucinyl]amino]-pyrrolidine bis hydrochloride

Following the procedure of Example 9(d) except substituting the compound of Example 14(c), the title compound was produced: MS(ES+) 290.3 (MH+).

e.) 1-benzyl-(3S)-[[N$^\alpha$-(2-naphthylacetonoyl)-L-leucinyl]amino]-pyrrolidine Following the procedure of Example 9(e) except substituting the compound of Example 14(d), the title compound was produced: MS(ES+) 458.4 (MH+).

Example 15

Preparation of 1-benzyl-(3S)-[[N$^\alpha$-(2-naphthylcarbonyl)-L-leucinyl]amino]-pyrrolidine Following the procedure of Example 14(e) except substituting 2-naphthoic acid for 2-naphthylacetic acid, the title compound was produced: MS(ES+) 444.4 (MH+).

Example 16

Preparation of 1-benzyl-(3S)-[[N$^\alpha$-(3-quinolinecarbonyl)-L-leucinyl]amino]-pyrrolidine Following the procedure of Example 14(e) except substituting 3-quinolinecarboxylic acid for 2-naphthylacetic acid, the title compound was produced: MS(ES+) 445.2 (MH+).

Example 17

Preparation of 1-benzyl-(3S)-[[N$^\alpha$-(2-quinolinecarbonyl)-L-leucinyl]amino]-pyrrolidine Following the procedure of Example 14(e) except substituting quinaldic acid for 2-naphthylacetic acid, the title compound was produced: MS(ES+) 445.3 (MH$^+$).

Example 18

Preparation of 1-benzyl-(3S)-[[N$^\alpha$-(3-isoquinolinecarbonyl)-L-leucinyl]amino]-pyrrolidine Following the procedure of Example 14(e) except substituting 3-isoquinolinecarboxylic acid for 2-naphthylacetic acid, the title compound was produced: MS(ES+) 445.3 (MH$^+$).

Example 19

Preparation of 1-benzyl-4-[[N$^\alpha$-(2-naphthylcarbonyl)-L-leucinyl]amino]-piperidine a.) 1-benzyl-4-[[N$^\alpha$-(tert-butoxycarbonyl)-L-leucinyl]amino]-piperidine Following the procedure of Example 1(c) except substituting 4-amino-1-benzylpiperidine, the title compound was produced: MS(ES+) 404.1 (MH$^+$).

b.) 1-benzyl-4-[(L-leucinyl]amino]-piperidine

The compound of Example 19(a) (2.0 g) was dissolved in 4N HCl/dioxane (100 mL). The reaction was stirred at room temperature for 30 minutes whereupon it was concentrated in vacuo to give 1.94 g of the title compound as a white solid: MS(ES+) 304.2 (MH$^+$).

c.) 1-benzyl-4-[[N$^\alpha$-(2-naphthylcarbonyl)-L-leucinyl]amino]-piperidine

To a solution of the compound of Example 19(b) (240 mg) in DMF (3.0 mL) was added N-methylmorpholine (0.17 mL), HOBT (101.5 mg), 2-naphthoic acid (130.2 mg) and EDC (145.4 mg). The reaction was stirred overnight whereupon it was poured into a rapidly stirred mixture of EtOAc, 10% Na$_2$CO$_3$ and brine (75 mL each). This mixture was stirred for 30 minutes. The organic layer was sepaerated and the aqueous layer was washed with ethyl acetate. The combined organic layers were washed with 10% Na$_2$CO$_3$, water, brine, dried (MgSO$_4$), filtered, concentrated and chromatographed (ethyl acetate) to give 107 mg of the title compound: MS(ES+) 458.5 (MH$^+$).

Example 20

Preparation of 1-benzyl-4-[[N$^\alpha$-(2-quinolinecarbonyl)-L-leucinyl]amino]-piperidine Following the procedure of Example 19(c) except substituting quinaldic acid for 2-naphthoic acid, the title compound was prepared: MS(ES+) 459.3 (MH$^+$).

Example 21

Preparation of 1-benzyl-4-[[N$^\alpha$-(benzyloxycarbonyl)-L-leucinyl]amino]-piperidine To a solution of N-benzyl-4-amino piperidine (0.50 g) in CH$_2$Cl$_2$ (10 mL) was added CBZ-leucine (695 mg), EDC (552.5 mg) and HOBT (356.6 mg). The reaction was stirred at room temperature until complete as indicated by TLC analysis. The reaction was dissolved in CHCl$_3$ and washed with 10% Na$_2$CO$_3$, brine, dried (MgSO$_4$), filtered, concentrated and chromatographed (3:1 EtOAc:hexanes) to give 0.99 g of the title compound: MS(ES+) 438 (MH$^+$).

Example 22

Preparation of 1-[3-(2-pyridyl)phenyl]-2-ethyl-(3S)-[[N$^\alpha$-(2-naphthylcarbonyl)-L-leucinyl]amino]-pyrrolidine a) N-methyl-N-methoxy-3-(2-pyridyl)-phenylacetamide To a stirred solution of N-methoxy-N-methylamine hydrochloride (0.980 g, 10.0 mmol) in DMF (25 mL) was added N-methylmorpholine (1.21 mL, 11.0 mmol), HOBt (1.50 g, 11.1 mmol), 3-(2-pyridyl)-phenylacetic acid (2.36 g, 11.1 mmol), and EDC (2.13 g, 11.1 mmol). The reaction was stirred overnight whereupon it was poured into a rapidly-stirred mixture of 150 mL each of EtOAc, 10% NaHCO$_3$, and brine. After stirring for 30 min, the layers were separated and the aqueous layer was washed with fresh EtOAc (150 mL). The combined organic layers were washed with 10% Na$_2$CO$_3$, and brine, then dried (MgSO$_4$), filtered, and concentrated. Column chromatography (silica gel, 3:1 EtOAc:hexane) gave 2.275 g of the title compound: MS (ES+) (MH+) 257.2.

b) 3-(2-pyridyl)-phenylacetaldehyde

To a stirred solution of the compound of Example 22(a) (2.2 g, 8.6 mmol) in anhydrous THF (20 mL) at −78° C. was added a solution of lithium aluminum hydride in THF (22 mL, 22.0 mmol). The reaction was stirred for 2 h, then warmed to 0° C. and stirred 1 h, whereupon 4.2 g of KHSO$_4$ was added in small portions over 10 min, followed by 100 mL of water in small portions. The reaction mixture was filtered to remove a white precipitate and the filtrate was adjusted to pH 9 by the addition of 1 N NaOH, then extracted with Et$_2$O (3×100 mL). The combined organic layers were washed with brine, then dried (Na$_2$SO$_4$), filtered, and concentrated to give 1.878 g of the title compound: MS (ES+) (MH+) 198.1.

c) 1-[3-(2-pyridyl)phenyl]-2-ethyl-(3S)-[N$^\alpha$-(tert-butoxycarbonylamino]-pyrrolidine To a stirred solution of (3S)-(−)-3-(tert-butoxycarbonylamino)pyrrolidine (672.3 mg, 3.6 mmol) in CH$_2$Cl$_2$ (15 mL) was added the compound of Example 22(b) (0.94 g, 4.3 mmol). The reaction was stirred 2 h whereupon Na(OAc)$_3$BH (1.68 g, 7.9 mmol) added. After stirring overnight, the reaction mixture was diluted with CHCl$_3$ (150 mL) and washed with H$_2$O, and brine, then dried (MgSO$_4$), filtered, and concentrated. Column chromatography (silica gel, 1:9 MeOH:EtOAc) gave 467 mg of the title compound: MS (ES+) (MH+) 368.

d) 1-[3-(2-pyridyl)phenyl]-2-ethyl-(3S)-[[N$^\alpha$-(tert-butoxycarbonyl)-L-leucinyl]amino]-pyrrolidine The compound of Example 22(c) (440 mg, 1.2 mmol) was dissolved in 4.0 N HCl in dioxane (20 mL) and stirred at room temperature for 30 min. The solution was concentrated to a white solid and dried under high vacuum for 30 min. To a stirred solution of the residue in DMF (10 mL) was added N-methylmorpholine (400 uL, 3.6 mmol), HOBt (245.6 mg, 1.8 mmol), Boc-Leucine hydrate (449.1 mg, 1.8 mmol), and EDC (352.0 mg, 1.8 mmol). The reaction was stirred overnight whereupon it was partitioned between 50 mL each of EtOAc, 10% $Na_2CO_3$, and brine. The aqueous layer was washed with fresh EtOAc (50 mL), the combined organic layers were washed with 10% $Na_2CO_3$ and brine, then dried ($MgSO_4$), filtered, and concentrated. Column chromatography (silica gel, 5:95 MeOH:EtOAc) gave 204 mg of the title compound: MS (ES+) (MH+) 481.4.

e) 1-[3-(2-pyridyl)phenyl]-2-ethyl-(3S)-[[$N^\alpha$-L-leucinyl]amino]-pyrrolidine dihydrochloride The compound of Example 22(d) (200 mg, 0.42 mmol) was dissolved in 4.0 N HCl in dioxane (25 mL) and stirred at room temperature for 1 h. The solution was concentrated to a white solid and dried under high vacuum for 3 h to give the title compound: MS (ES+) (MH+) 381.4.

f) 1-[3-(2-pyridyl)phenyl]-2-ethyl-(3S)-[[$N^\alpha$-(2-naphthylcarbonyl)-L-leucinyl]amino]-pyrrolidine To a stirred solution of the compound of Example 22(e) (0.14 mmol) in DMF (2 mL) was added N-methylmorpholine (62 uL, 0.56 mmol), HOBt (31.8 mg, 0.24 mmol), 2-naphthoic acid (37.6 mg, 0.22 mmol), and EDC (41.2 mg, 0.22 mmol). The reaction was stirred overnight whereupon it was partitioned between 50 mL each of EtOAc, 10% $Na_2CO_3$, and brine. The aqueous layer was washed with fresh EtOAc (50 mL), the combined organic layers were washed with 10% $Na_2CO_3$ and brine, then dried ($MgSO_4$), filtered, and concentrated. Column chromatography (silica gel, 5:95 MeOH:EtOAc) gave 40.1 mg of the title compound: MS (ES+) (MH+) 535.4.

Example 23

Preparation of 1-[3-(2-pyridyl)phenyl]-2-ethyl-(3S)-[[$N^\alpha$-(2-quinolinecarbonyl)-L-leucinyl]amino]-pyrrolidine Following the procedure of Example 22(f), except using 2-quinolinecarboxylic acid, the title compound was prepared: MS (ES+) (MH+) 536.4.

Example 24

Preparation of 1-[3-(2-pyridyl)phenyl]-2-ethyl-(3S)-[[$N^\alpha$-(3-isoquinolinecarbonyl-L-leucinyl]amino]-pyrrolidine Following the procedure of Example 22(f), except using 3-isoquinolinecarboxylic acid, the title compound was prepared: MS (ES+) (MH+) 536.4.

Example 25

Preparation of 1-[3-(2-pyridyl)phenyl]-2-ethyl-(3R)-[[$N^\alpha$-(2-naphthylcarbonyl)-L-leucinyl]amino]-pyrrolidine a) 1-[3-(2-pyridyl)phenyl]-2-ethyl-(3R)-[$N^\alpha$-(tert-butoxycarbonylamino]-pyrrolidine Following the procedure of Example 22(c), except substituting (3R)-(+)-3-(tert-butoxycarbonylamino)pyrrolidine, the title compound was prepared: MS (ES+) (MH+) 368.4.

b) 1-[3-(2-pyridyl)phenyl]-2-ethyl-(3R)-[[$N^\alpha$-(tert-butoxycarbonyl)-L-leucinyl]amino]-pyrrolidine Following the procedure of Example 22(d), except substituting the compound of Example 25(a), the title compound was prepared: MS (ES+) (MH+) 481.4.

c) 1-[3-(2-pyridyl)phenyl]-2-ethyl-(3R)-[[$N^\alpha$-L-leucinyl]amino]-pyrrolidine dihydrochloride Following the procedure of Example 22(e), except substituting the compound of Example 25(b), the title compound was prepared: MS (ES+) (MH+) 381.4.

d) 1-[3-(2-pyridyl)phenyl]-2-ethyl-(3R)-[[$N^\alpha$-(2-naphthylcarbonyl)-L-leucinyl]amino]-pyrrolidine Following the procedure of Example 22 (f), except substituting the compound of Example 25 (c), the title compound was prepared: MS (ES+) (MH+) 535.3.

Example 26

Preparation of 1-[3-(2-pyridyl)phenyl]-2-ethyl-(3R)-[[$N^\alpha$-(3-isoquinolinecarbonyl)-L-leucinyl]amino]-pyrrolidine Following the procedure of Example 25(d), except using 3-isoquinolinecarboxylic acid, the title compound was prepared: MS (ES+) (MH+) 536.3.

Example 27

Preparation of 1-[3-(2-pyridyl)phenyl]-2-ethyl-(3R)-[[$N^\alpha$(-(2-quinolinecarbonyl)-L-leucinyl]amino]-pyrrolidine Following the procedure of Example 25(d), except using 2-quinolinecarboxylic acid, the title compound was prepared: MS (ES+) (MH+) 536.3.

Example 28

Preparation of 1-(1-adamantanecarbonyl)-(3R)-[[$N^\alpha$-(4-pyridylmethoxycarbonyl)-L-leucinyl]amino]-pyrrolidine a) 1-(1-adamantanecarbonyl)-(3R)-[[$N^\alpha$-(tert-butyloxycarbonyl)-L-leucinyl]amino]-pyrrolidine To a stirred solution of (3R)-(+)-3-(tert-butoxycarbonylamino)pyrrolidine (1.87 g, 10.0 mmol) in $CH_2Cl_2$ (30 mL) at 0° C. was added N-methylmorpholine (1.65 mL, 15.0 mmol) and 1-adamantylcarbonyl chloride (2.99 g, 15.0 mmol). The reaction was stirred overnight, gradually warming to room temperature, whereupon it was diluted with 200 mL of $CHCl_3$, washed with 5% $NaHCO_3$, $H_2O$, 1N HCl, $H_2O$, and brine, then dried ($MgSO_4$), filtered, and concentrated to give 4.66 g of the title compound: MS (ES+) (MH+) 349.4.

b) 1-(1-adamantanecarbonyl)-(3R)-aminopyrrolidine hydrochloride

The compound of Example 28 (a) (4.6 g) was dissolved in 4.0 N HCl in dioxane (100 mL) and stirred at room temperature for 1 h. The solution was concentrated to a white solid and dried under high vacuum for 2 h to give the title compound: MS (ES+) (MH+) 249.1.

c) 1-(1-adamantanecarbonyl)-(3R)-[[$N^\alpha$-(4-pyridylmethoxycarbonyl)-L-leucinyl]amino]-pyrrolidine To a stirred solution of the compound of Example 28(b) (143.2 mg, 0.50 mmol) in DMF (2 mL) was added N-methylmorpholine (83 uL, 0.75 mmol), HOBt (101.5 mg, 0.75 mmol), 4-Inoc-Leucine (201.5 mg, 0.76 mmol), and EDC (146.0 mg, 0.76 mmol). The reaction was stirred overnight whereupon it was partitioned between 50 mL each of EtOAc, 10% Na$_2$CO$_3$, and brine. The aqueous layer was washed with fresh EtOAc (50 mL), the combined organic layers were washed with 10% Na$_2$CO$_3$ and brine, then dried (MgSO$_4$), filtered, and concentrated. Column chromatography (silica gel, 2:98 MeOH:EtOAc) gave 109.0 mg of the title compound: MS (ES+) (MH+) 497.5.

Example 29

Preparation of 1-(1-adamantanecarbonyl)-(3S)-[[N$^\alpha$-(4-pyridylmethoxycarbonyl)-L-leucinyl]amino]-pyrrolidine a) 1-(1-adamantanecarbonyl)-(3S)-[[N$^\alpha$-(tert-butyloxycarbonyl)-L-leucinyl]amino]-pyrrolidine Following the procedure of Example 28(a), except substituting (3S)-(−)-3-(tert-butoxycarbonylamino)pyrrolidine, the title compound was prepared: MS (ES+) (MH+) 349.5.

b) 1-(1-adamantanecarbonyl)-(3S)-aminopyrrolidine hydrochloride

Following the procedure of Example 28(b), except substituting the compound of Example 29 (a), the title compound was prepared: MS (ES+) (MH+) 249.1.

c) 1-(1-adamantanecarbonyl)-(3S)-[[N$^\alpha$-(4-pyridylmethoxycarbonyl)-L-leucinyl]amino]-pyrrolidine Following the procedure of Example 28(c), except substituting the compound of Example 29(b), the title compound was prepared: MS (ES+) (MH+) 497.4.

Example 30

Preparation of (3R)-[[N$^\alpha$-(benzo[b]thiophene-2-carbonyl)-L-leucinyl]amino]-1-[(2S)-4-methyl-2-[[(benzyloxycarbonyl)amino]pentyl]-pyrrolidine a) (3R)-[[N$^\alpha$-(tert-butoxycarbonyl)amino]-1-[(2S)-4-methyl-2-[[(benzyloxycarbonyl)amino]pentyl]-pyrrolidine To a stirred solution of (3R)-(+)-3-(tert-butoxycarbonylamino)pyrrolidine (2 g, 10.7 mmol) in CH$_2$Cl$_2$ (200 mL) was added N-CBZ-Leucinal (3.2 g, 12.9 mmol). The reaction was stirred 2 h whereupon Na(OAc)$_3$BH (3.4 g, 16.1 mmol) was added. After stirring overnight, the reaction mixture was diluted with CHCl$_3$ (150 mL) and washed with 5% NaHCO$_3$ and brine, then dried (MgSO$_4$), filtered, and concentrated. Column chromatography (silica gel, 3:97 MeOH:CH$_2$Cl$_2$) gave 3.4 g of the title compound: MS (ES+) (MH+) 420.

b) (3R)-amino-1-[(2S)-4-methyl-2-[[(benzyloxycarbonyl)amino]pentyl]-pyrrolidine dihydrochloride The compound of Example 30 (a) (3.4 g) was dissolved in 4.0 N HCl in dioxane (50 mL) and stirred at room temperature for 1 h. The solution was concentrated in vacuo and dried under high vacuum to give 3.37 g of the title compound: MS (ES+) (MH+) 320.

c) (3R)-[[N$^\alpha$-(tert-butoxycarbonyl)-L-leucinyl]amino]-1-[(2S)-4-methyl-2-[[(benzyloxycarbonyl)amino]pentyl]-pyrrolidine To a stirred solution of the compound of Example 30(b) (2.36 g, 6.0 mmol) in DMF (25 mL) was added N-methylmorpholine (2.0 mL, 18.2 mmol), HOBt (1.22 g, 9.0 mmol), Boc-Leucine hydrate (2.25 g, 9.0 mmol), and EDC (1.73 g, 9.0 mmol). The reaction was stirred for 3 h whereupon it was partitioned between 150 mL each of EtOAc, 10% Na$_2$CO$_3$, and brine. The aqueous layer was washed with fresh EtOAc (150 mL), the combined organic layers were washed with 10% Na$_2$CO$_3$ and brine, then dried (MgSO$_4$), filtered, and concentrated. Column chromatography (silica gel, 2:1 EtOAc:hexane) gave 2.78 g of the title compound: MS (ES+) (MH+) 533.6.

d) (3R)-[[N$^\alpha$-L-leucinyl]amino]-1-[(2S)-4-methyl-2-[[(benzyloxycarbonyl)amino]pentyl]-pyrrolidine dihydrochloride The compound of Example 30(c) (2.7 g) was dissolved in 4.0 N HCl in dioxane (100 mL) and stirred at room temperature for 1 h. The solution was concentrated in vacuo and dried azeotropically with toluene to afford a tan solid and stored under high vacuum overnight to give 2.45 g of the title compound: MS (ES+) (MH+) 433.3.

e) (3R)-[[N$^\alpha$-(benzo[b]thiophene-2-carbonyl)-L-leucinyl]amino]-1-[(2S)-4-methyl-2-[[(benzyloxycarbonyl)amino]pentyl]-pyrrolidine To a stirred solution of the compound of Example 30(d) (101.4 mg, 0.2 mmol) in DMF (1 mL) was added N-methylmorpholine (66 uL, 0.6 mmol), HOBt (42.2 mg, 0.3 mmol), benzo[b]thiophene-2-carboxylic acid (53.3 mg, 0.3 mmol), and EDC (57.8 mg, 0.3 mmol). The reaction was stirred overnight whereupon it was partitioned between 50 mL each of EtOAc, 10% Na$_2$CO$_3$, and brine. The aqueous layer was washed with fresh EtOAc (50 mL), the combined organic layers were washed with 10% Na$_2$CO$_3$ and brine, then dried (MgSO$_4$), filtered, and concentrated. Column chromatography (silica gel, 3:1 EtOAc:hexane) gave 80.4 mg of the title compound: MS (ES+) (MH+) 593.4.

Example 31

Preparation of (3R)-[[N$^\alpha$-(3,4-dimethoxybenzoyl)-L-leucinyl]amino]-1-[(2S)-4-methyl-2-[[(benzyloxycarbonyl)amino]pentyl]-pyrrolidine Following the procedure of Example 30(e), except substituting 3,4-dimethoxybenzoic acid, the title compound was prepared: MS (ES+) (MH+) 597.4.

Example 32

Preparation of (3R)-[[N$^\alpha$-(benzofuran-2-carbonyl)-L-leucinyl]amino]-1-(2S)-4-methyl-2-[[(benzyloxycarbonyl)amino]pentyl]-pyrrolidine Following the procedure of Example 30(e), except substituting benzofuran-2-carboxylic acid, the title compound was prepared: MS (ES+) (MH+) 577.2.

Example 33

Preparation of (3R)-[[N$^\alpha$-(benzothiazole-6-carbonyl)-L-leucinyl]amino]-1-[(2S)-4-methyl-2-[[(benzyloxycarbonyl)amino]pentyl]-pyrrolidine Following the procedure of Example 30(e), except substituting benzothiazole-6-carboxylic acid, the title compound was prepared: MS (ES+) (MH+) 594.4.

Example 34

Preparation of (3R)-[[N$^\alpha$-(indole-2-carbonyl)-L-leucinyl]amino]-1-[(2S)-4-methyl-2-[[(benzyloxycarbonyl)amino]pentyl]-pyrrolidine Following the procedure of Example 30(e), except substituting indole-2-carboxylic acid, the title compound was prepared: MS (ES+) (MH+) 576.3.

Example 35

Preparation of (3R)-[[N$^\alpha$-(4-fluorobenzoyl)-L-leucinyl]amino]-1-[(2S)-4-methyl-2-[[(benzyloxycarbonyl)amino]pentyl]-pyrrolidine Following the procedure of Example 30(e), except substituting 4-fluorobenzoic acid, the title compound was prepared: MS (ES+) (MH+) 555.3.

Example 36

Preparation of (3R)-[[N$^\alpha$-(4-methoxybenzoyl)-L-leucinyl]amino]-1-[(2S)-4-methyl-2-[[(benzyloxycarbonyl)amino]pentyl]-pyrrolidine Following the procedure of Example 30(e), except substituting p-4-methoxybenzoic acid, the title compound was prepared: MS (ES+) (MH+) 567.4.

Example 37

Preparation of (3R)-[[N$^\alpha$-(3,4-dichlorobenzoyl)-L-leucinyl]amino]-1-[(2S)-4-methyl-2-[[(benzyloxycarbonyl)amino]pentyl]-pyrrolidine Following the procedure of Example 1(e), except substituting 3,4-dichlorobenzoic acid, the title compound was prepared: MS (ES+) (MH+) 605.2.

Example 38

Preparation of (3R)-[[N$^\alpha$-(thiophene-2-carbonyl)-L-leucinyl]amino]-1-[(2S)-4-methyl-2-[[(benzyloxycarbonyl)amino]pentyl]-pyrrolidine Following the procedure of Example 30(e), except substituting thiophene-3-carboxylic acid, the title compound was prepared: MS (ES+) (MH+) 543.4.

Example 39

Preparation of (3R)-[[N$^\alpha$-(4-biphenylcarbonyl)-L-leucinyl]amino]-1-[(2S)-4-methyl-2-[[(benzyloxycarbonyl)amino]pentyl]-pyrrolidine To a stirred solution of the compound of Example 30(d) (102.3 mg, 0.2 mmol) in CH$_2$Cl$_2$ (1 mL) at 0° C. was added N-methylmorpholine (66 uL, 0.6 mmol) and 4-biphenylcarbonyl chloride (65.2 mg, 0.3 mmol). The reaction was stirred overnight whereupon it was diluted with CHCl$_3$ and washed with 10% Na$_2$CO$_3$ and brine, then dried (MgSO$_4$), filtered, and concentrated. Column chromatography (silica gel, 3:1 EtOAc:hexane) gave 55.1 mg of the title compound: MS (ES+) (MH+) 613.5.

Example 40

Preparation of (3R)-[[N$^\alpha$-(5-methoxybenzofuran-2-carbonyl)-L-leucinyl]amino]-1-[(2S)-4-methyl-2-[[(benzyloxycarbonyl)amino]pentyl]-pyrrolidine Following the procedure of Example 30(e), except substituting 5-methoxybenzofuran-2-carboxylic acid, the title compound was prepared: MS (ES+) (MH+) 607.4.

Example 41

Preparation of (3R)-[[N$^\alpha$-(5-chlorobenzofuran-2-carbonyl)-L-leucinyl]amino]-1-[(2S)-4-methyl-2-[[(benzyloxycarbonyl)amino]pentyl]-pyrrolidine Following the procedure of Example 30(e), except substituting 5-chlorobenzofuran-2-carboxylic acid, the title compound was prepared: MS (ES+) (MH+) 611.4.

Example 42

Preparation of (3R)-[[N$^\alpha$-(7-methoxybenzofuran-2-carbonyl)-L-leucinyl]amino]-1-[(2S)-4-methyl-2-[[(benzyloxycarbonyl)amino]pentyl]-pyrrolidine Following the procedure of Example 30(e), except substituting 7-methoxybenzofuran-2-carboxylic acid, the title compound was prepared: MS (ES+) (MH+) 607.4.

Example 43

Preparation of (3R)-[[N$^\alpha$-(3-chlorobenzo[b]thiophene-2-carbonyl)-L-leucinyl]amino-1-[(2S)-4-methyl-2-[[(benzyloxycarbonyl)amino]pentyl]-pyrrolidine Following the procedure of Example 30(e), except substituting 3-chlorobenzo[b]thiophene-2-carboxylic acid, the title compound was prepared: MS (ES+) (MH+) 627.3.

Example 44

Preparation of (3R)-[[N$^\alpha$-(3-(2-pyridyl)benzoyl)-L-leucinyl]amino]-1-[(2S)-4-methyl-2-[[(benzyloxycarbonyl)amino]pentyl]-pyrrolidine Following the procedure of Example 30(e), except substituting 3-(2-pyridyl)benzoic acid, the title compound was prepared: MS (ES+) (MH+) 614.4.

Example 45

Preparation of (3S)-[[N$^\alpha$-(benzo[b]thiophene-2-carbonyl)-L-leucinyl]amino]-1-[(2S)-4-methyl-2-[[(benzyloxycarbonyl)amino]pentyl]-pyrrolidine a) (3S)-[[N$^\alpha$-(tert-butoxycarbonyl)amino]-1-[(2S)-4-methyl-2-[[(benzyloxycarbonyl)amino]pentyl]-pyrrolidine Following the procedure of Example 30(a), except substituting (3S)-(−)-3-(tert-butoxycarbonylamino)pyrrolidine, the title compound was prepared: MS (ES+) (MH+) 420.

b) (3S)-amino-[(2S)-4-methyl-2-[[(benzyloxycarbonyl)amino]pentyl]-pyrrolidine dihydrochloride Following the procedure of Example 30(b), except substituting the compound of Example 45(a), the title compound was prepared: MS (ES+) (MH+) 320.

c) (3S)-[[N$^\alpha$-(tert-butoxycarbonyl)-L-leucinyl]amino]-1-[(2S)-4-methyl-2-[[(benzyloxycarbonyl)amino]pentyl]-pyrrolidine Following the procedure of Example 30(c), except substituting the compound of Example 45(b), the title compound was prepared: MS (ES+) (MH+) 533.5.

d) (3S)-[[N$^\alpha$-L-leucinyl]amino]-1-[(2S)-4-methyl-2-[[(benzyloxycarbonyl)amino]pentyl]-pyrrolidine dihydrochloride Following the procedure of Example 30(d), except substituting the compound of Example 45(c), the title compound was prepared: MS (ES+) (MH+) 433.3.

e) (3S)-[[N$^\alpha$-(benzo[b]thiophene-2-carbonyl)-L-leucinyl]amino]-1-[(2S)-4-methyl-2-[[(benzyloxycarbonyl)amino]pentyl]-pyrrolidine Following the procedure of Example 30(e), except substituting the compound of Example 45(d), the title compound was prepared: MS (ES+) (MH+) 593.4.

Example 46

Preparation of (3S)-[[N$^\alpha$-(3,4-dimethoxybenzoyl)-L-leucinyl]amino]-1-[(2S)-4-methyl-2-[[(benzyloxycarbonyl)amino]pentyl]-pyrrolidine Following the procedure of Example 45(e), except substituting 3,4-dimethoxybenzoic acid, the title compound was prepared: MS (ES+) (MH+) 597.5.

Example 47

Preparation of (3S)-[[N$^\alpha$-(benzofuran-2-carbonyl)-L-leucinyl]amino]-1-[(2S)-4-methyl-2-[[(benzyloxycarbonyl)amino]pentyl]-pyrrolidine Following the procedure of Example 45(e), except substituting benzofuran-2-carboxylic acid, the title compound was prepared: MS (ES+) (MH+) 577.4.

Example 48

Preparation of (3S)-[[N$^\alpha$-(benzothiazole-6-carbonyl)-L-leucinyl]amino]-1-[(2S)-4-methyl-2-[[(benzyloxycarbonyl)amino]pentyl]-pyrrolidine Following the procedure of Example 45(e), except substituting benzothiazole-6-carboxylic acid, the title compound was prepared: MS (ES+) (MH+) 594.4.

Example 49

Preparation of (3S)-[[N$^\alpha$-(indole-2-carbonyl)-L-leucinyl]amino]-1-[(2S)-4-methyl-2-[[(benzyloxycarbonyl)amino]pentyl]-pyrrolidine Following the procedure of Example 45(e), except substituting indole-2-carboxylic acid, the title compound was prepared: MS (ES+) (MH+) 576.4.

Example 50

Preparation of (3S)-[[N$^\alpha$-(4-fluorobenzoyl)-L-leucinyl]amino]-1-[(2S)-4-methyl-2-[[(benzyloxycarbonyl)amino]pentyl]-pyrrolidine Following the procedure of Example 45(e), except substituting 4-fluorobenzoic acid, the title compound was prepared: MS (ES+) (MH+) 555.3.

Example 51

Preparation of (3S)-[[N$^\alpha$-(4-methoxybenzoyl)-L-leucinyl]amino]-1-[(2S)-4-methyl-2-[[(benzyloxycarbonyl)amino]pentyl]-pyrrolidine Following the procedure of Example 45(e), except substituting p-4-methoxybenzoic acid, the title compound was prepared: MS (ES+) (MH+) 567.3.

Example 52

Preparation of (3S)-[[N$^\alpha$-(3,4-dichlorobenzoyl)-L-leucinyl]amino]-1-[(2S)-4-methyl-2-[[(benzyloxycarbonyl)amino]pentyl]-pyrrolidine Following the procedure of Example 45(e), except substituting 3,4-dichlorobenzoic acid, the title compound was prepared: MS (ES+) (MH+) 605.2.

Example 53

Preparation of (3S)-[[N$^\alpha$-(thiophene-2-carbonyl)-L-leucinyl]amino]-1-[(2S)-4-methyl-2-[[(benzyloxycarbonyl)amino]pentyl]-pyrrolidine Following the procedure of Example 45(e), except substituting thiophene-3-carboxylic acid, the title compound was prepared: MS (ES+) (MH+) 543.2.

Example 54

Preparation of (3S)-[[N$^\alpha$-(4-biphenylcarbonyl)-L-leucinyl]amino]-1-[(2S)-4-methyl-2-[[(benzyloxycarbonyl)amino]pentyl]-pyrrolidine Following the procedure of Example 39, except substituting the compound of Example 45(e), the title compound was prepared: MS (ES+) (MH+) 613.4.

Example 55

Preparation of (3S)-[[N$^\alpha$-(5-methoxybenzofuran-2-carbonyl)-L-leucinyl]amino]-1-[(2S)-4-methyl-2-[[(benzyloxycarbonyl)amino]pentyl]-pyrrolidine Following the procedure of Example 45(e), except substituting 5-methoxybenzofuran-2-carboxylic acid, the title compound was prepared: MS (ES+) (MH+) 607.4.

Example 56

Preparation of (3S)-[[N$^\alpha$-(5-chlorobenzofuran-2-carbonyl)-L-leucinyl]amino]-1-[(2S)-4-methyl-2-[[(benzyloxycarbonyl)amino]pentyl]-pyrrolidine Following the procedure of Example 45(e), except substituting 5-chlorobenzofuran-2-carboxylic acid, the title compound was prepared: MS (ES+) (MH+) 611.4.

Example 57

Preparation of (3S)-[[N$^\alpha$-(7-methoxybenzofuran-2-carbonyl)-L-leucinyl]amino]-1-[(2S)-4-methyl-2-[[(benzyloxycarbonyl)amino]pentyl]-pyrrolidine Following the procedure of Example 45(e), except substituting 7-methoxybenzofuran-2-carboxylic acid, the title compound was prepared: MS (ES+) (MH+) 607.4.

Example 58

Preparation of (3S)-[[N$^\alpha$-(3-chlorobenzo[b]thiophene-2-carbonyl)-L-leucinyl]amino]-1-[(2S)-4-methyl-2-[[(benzyloxycarbonyl)amino]pentyl]-pyrrolidine Following the procedure of Example 45(e), except substituting 3-chlorobenzo[b]thiophene-2-carboxylic acid, the title compound was prepared: MS (ES+) (MH+) 627.2.

Example 59

Preparation of (3S)-[[N$^\alpha$-(3-(2-pyridyl)benzoyl)-L-leucinyl]amino]-1-[(2S)-4-methyl-2-[[(benzyloxycarbonyl)amino]pentyl]-pyrrolidine Following the procedure of Example 45(e), except substituting 3-(2-pyridyl)benzoic acid, the title compound was prepared: MS (ES+) (MH+) 614.4.

Example 60

Preparation of 1-(4-phenyl)benzyl-(3S)-[[N$^\alpha$-(tert-butoxycarbonyl)-L-leucinyl]amino]-pyrrolidine a) 1-(2,2,2-trichloroethylcarbonyl)-(3S)-[[N$^\alpha$-(tert-butoxycarbonyl)amino]-pyrrolidine To a stirred solution of (3S)-(−)-3-(tert-butoxycarbonylamino)pyrrolidine (10 g, 53.7 mmol) in CH$_2$Cl$_2$ (150 mL) at 0° C. was added N-methylmorpholine (6.50 mL, 59.1 mmol), and 2,2,2-trichloroethyl chloroformate (8.20 mL, 59.6 mmol). After stirring overnight, gradually warming to room temperature, the reaction mixture was concentrated to 1/2 original volume, diluted with $CHCl_3$ (250 mL), and washed with 5% $NaHCO_3$, $H_2O$, 1N HCl, $H_2O$, and brine, then dried ($MgSO_4$), filtered, and concentrated to give 23.98 g of the title compound: $^1$H-NMR (400 MHz, $CDCl_3$): d (ppm) 4.74 (s, 2H); 4.66 (br m, 1H); 4.25 (br m, 1H); 3.72 (m, 1H); 3.56 (m, 2H); 3.33 (m, 1H); 2.19 (m, 1H); 1.87 (m, 1H); 1.45 (s, 9H).

b) 1-(2,2,2-trichloroethylcarbonyl)-(3S)-[[N$^\alpha$-(tert-butoxycarbonyl)-L-leucinyl]amino]-pyrrolidine The compound of Example 60(a) (23.9 g) was dissolved in 4.0 N HCl in dioxane (200 mL) and stirred at room temperature for 1 h. The solution was concentrated to a white solid and stored under high vacuum for 30 min. To a stirred solution of the residue in DMF (200 mL) was added N-methylmorpholine (8.90 mL, 80.9 mmol), HOBt (10.88 g, 80.5 mmol), Boc-Leucine hydrate (20.09 g, 80.6 mmol), and EDC (15.44 g, 80.6 mmol). The reaction was stirred overnight whereupon it was partitioned between EtOAc (300 mL), 10% $Na_2CO_3$ (150 mL), and brine (150 mL). The aqueous layer was washed with fresh EtOAc (100 mL), the combined organic layers were washed with 1N HCl, $H_2O$, 10% $Na_2CO_3$, $H_2O$, and brine, then dried ($MgSO_4$), filtered, and concentrated to give 27.88 g of the title compound: MS (ES+) (MH+) 474.1.

c) (3S)-[[N$^\alpha$-(tert-butoxycarbonyl)-L-leucinyl]amino]-pyrrolidine

To a stirred solution of the compound of Example 60(b) (27.7 g) in THF (200 mL) was added a solution of 1N $NH_4OAc$ (pH 7–7.5, 40 mL), followed by Zn powder (25.06 g). The reaction was stirred for 3 h at room temperature whereupon the slurry was filtered through a pad of Celite, followed by several $CHCl_3$ washes. The combined filtrates were concentrated to remove THF, diluted with additional $CHCl_3$ (300 mL) and washed with 10% $Na_2CO_3$ and brine, then dried ($MgSO_4$), filtered, and concentrated to give 16.34 g of the title compound: MS (ES+) (MH+) 300.2.

d) 1-(4-phenyl)benzyl-(3S)-[[N$^\alpha$-t-(tert-butoxycarbonyl)-L-leucinyl]amino]-pyrrolidine To a stirred solution of the compound of Example 60(c) (1.51 g, 5.0 mmol) in $CH_2Cl_2$ (10 mL) was added 4,4'-biphenylcarboxaldehyde (1.09 g, 6.0 mmol). The reaction was stirred 2 h whereupon Na(OAc)$_3$ (2.34 g, 11.0 mmol) was added. After stirring overnight, the reaction mixture was diluted with $CHCl_3$ (100 mL) and washed with 5% $NaHCO_3$ and brine, then dried ($MgSO_4$), filtered, and concentrated. Column chromatography (silica gel, 2:1 EtOAc:hexane to 3:1 EtOAc:hexane) gave 1.68 g of the title compound: MS (ES+) (MH+) 466.4.

Example 61

Preparation of 1-(4-phenyl)benzyl-(3S)-[[N$^\alpha$-(2-naphthylcarbonyl)-L-leucinyl]amino]-pyrrolidine a) 1-(4-phenyl)benzyl-(3S)-[[N$^\alpha$-L-leucinyl]amino]-pyrrolidine dihydrochloride The compound of Example 60(d) (1.57 g, 3.4 mmol) was dissolved in 4.0 N HCl in dioxane (25 mL) and stirred at room temperature for 1 h. The solution was concentrated to a white solid and dried under high vacuum for 30 min to give the title compound: MS (ES+) (MH+) 366.4.

b) 1-(4-phenyl)benzyl-(3S)-[[N-(2-naphthylcarbonyl)-L-leucinyl]amino]-pyrrolidine To a stirred solution of the compound of Example 61(a) (132.9 mg, 0.30 mmol) in DMF (1 mL) was added N-methylmorpholine (100 uL, 0.91 mmol), HOBt (62.0 mg, 0.46 mmol), 2-naphthoic acid (78.4 mg, 0.46 mmol), and EDC (87.3 mg, 0.46 mmol). The reaction was stirred overnight whereupon it was partitioned between 50 mL each of EtOAc, 10% $Na_2CO_3$, and brine. The aqueous layer was washed with fresh EtOAc (50 mL), the combined organic layers were washed with 10% $Na_2CO_3$ and brine, then dried ($MgSO_4$), filtered, and concentrated. Column chromatography (silica gel, 2:1 EtOAc:hexane) gave 102.8 mg of the title compound: MS (ES+) (MH+) 520.3.

Example 62

Preparation of 1-(4-phenyl)benzyl-(3S)-[[N$^\alpha$-(2-quinolinecarbonyl)-L-leucinyl]amino]-pyrrolidine Following the procedure of Example 61(b), except substituting 2-quinolinecarboxylic acid, the title compound was prepared: MS (ES+) (MH+) 521.3.

Example 63

Preparation of 1-(4-phenyl)benzyl-(3S)-[[N$^\alpha$-(3-dimethoxybenzoyl)-L-leucinyl]amino]-pyrrolidine Following the procedure of Example 61(b), except substituting 3,4-dimethoxybenzoic acid, the title compound was prepared: MS (ES+) (MH+) 530.3.

Example 64

Preparation of 1-(4-phenyl)benzyl-(3S)-[[N$^\alpha$-(benzofuran-2-carbonyl)-L-leucinyl]amino]-pyrrolidine Following the procedure of Example 61(b), except substituting benzofuran-2-carboxylic acid, the title compound was prepared: MS (ES+) (MH+) 510.3.

Example 65

Preparation of 1-(4-phenyl)benzyl-(3S)-[[N$^\alpha$-(benzo[b]thiophene-2-carbonyl)-L-leucinyl]amino]-pyrrolidine Following the procedure of Example 61(b), except substituting benzo[b]thiophene-2-carboxylic acid, the title compound was prepared: MS (ES+) (MH+) 526.4.

Example 66

Preparation of 1-(4-phenyl)benzyl-(3S)-[[N$^\alpha$-(benzyloxycarbonyl)-L-leucinyl]amino]-pyrrolidine To a stirred suspension of the compound of Example 61(a) (132.9 mg, 0.30 mmol) in $CH_2Cl_2$ (2 mL) at 0° C. was added N-methylmorpholine (132 uL, 1.20 mmol), and benzyl chloroformate (53 uL, 0.36 mmol). The reaction was stirred overnight, gradually warming to room temperature, whereupon it was diluted with $CHCl_3$ (100 mL) and washed with 10% $Na_2CO_3$ and brine, then dried ($MgSO_4$), filtered, and concentrated. Column chromatography (silica gel, EtOAc) gave 94.0 mg of the title compound: MS (ES+) (MH+) 500.3.

Example 67

Preparation of 1-(2-phenyl)ethyl-(3S)-[[N$^\alpha$-(tert-butoxycarbonyl)-L-leucinyl]amino]-pyrrolidine Following the procedure of Example 60(d), except substituting phenylacetaldehyde, the title compound was prepared: MS (ES+) (MH+) 404.4.

Example 68

Preparation of 1-(2-phenyl)ethyl-(3S)-[[N$^\alpha$-(2-naphthylcarbonyl)-L-leucinyl]amino]-pyrrolidine a) 1-(2-phenyl)ethyl-(3S)-[[N$^\alpha$-L-leucinyl]amino]-pyrrolidine dihydrochloride The compound of Example 67 (1.13 g, 2.8 mmol) was dissolved in 4.0 N HCl in dioxane (25 mL) and stirred at room temperature for 1 h. The solution was concentrated to a white solid and dried under high vacuum for 30 min to give the title compound: MS (ES+) (MH+) 304.3.

b) 1-(2-phenyl)ethyl-(3S)-[[N$^\alpha$-(2-naphthylcarbonyl)-L-leucinyl]amino]-pyrrolidine Following the procedure of Example 61(b), except substituting the compound of Example 68(a), the title compound was prepared: MS (ES+) (MH+) 458.3.

Example 69

Preparation of 1-(2-phenyl)ethyl-(3S)-[[N$^\alpha$-(2-quinolinecarbonyl)-L-leucinyl]amino]-pyrrolidine Following the procedure of Example 68(b), except substituting 2-quinolinecarboxylic acid, the title compound was prepared: MS (ES+) (MH+) 459.5.

Example 70

Preparation of 1-(2-phenyl)ethyl-(3S)-[[N$^\alpha$-(benzo[b]thiophene-2-carbonyl)-L-leucinyl]amino]-pyrrolidine Following the procedure of Example 68(b), except substituting benzo[b]thiophene-2-carboxylic acid, the title compound was prepared: MS (ES+) (MH+) 464.3.

Example 71

Preparation of 1-(2-phenyl)ethyl-(3S)-[[N$^\alpha$-(benzofuran-2-carbonyl)-L-leucinyl]amino]-pyrrolidine Following the procedure of Example 68(b), except substituting benzofuran-2-carboxylic acid, the title compound was prepared: MS (ES+) (MH+) 448.3.

Example 72

Preparation of 1-(2-phenyl)ethyl-(3S)-[[N$^\alpha$-(3-chlorobenzo[b]thiophene-2-carbonyl)-L-leucinyl]amino]-pyrrolidine Following the procedure of Example 68(b), except substituting 3-chlorobenzo[b]thiophene-2-carboxylic acid, the title compound was prepared: MS (ES+) (MH+) 498.1.

Example 73

Preparation of 1-(4-phenoxy)benzyl-(3S)-[[N$^\alpha$-(tert-butoxycarbonyl)-L-leucinyl]amino]-pyrrolidine Following the procedure of Example 60(d), except substituting 4-phenoxybenzaldehyde, the title compound was prepared: MS (ES+) (MH+) 482.4.

Example 74

Preparation of 1-(4-phenoxy)benzyl-(3S)-[[N$^\alpha$-(2-naphthylcarbonyl)-L-leucinyl]amino]-pyrrolidine a) 1-(4-phenoxy)benzyl-(3S)-[[N$^\alpha$-L-leucinyl]amino]-pyrrolidine dihydrochloride The compound of Example 73 (1.52 g, 3.2 mmol) was dissolved in 4.0 N HCl in dioxane (25 mL) and stirred at room temperature for 1 h. The solution was concentrated to a white solid and dried under high vacuum for 30 min to give the title compound: MS (ES+) (MH+) 382.4.

b) 1-(4-phenoxy)benzyl-(3S)-[[N$^\alpha$-(2-naphthylcarbonyl)-L-leucinyl]amino]-pyrrolidine Following the procedure of Example 61(b), except substituting the compound of Example 74(a), the title compound was prepared: MS (ES+) (MH+) 536.3.

Example 75

Preparation of 1-(4-phenoxy)benzyl-(3S)-[[N$^\alpha$-(2-quinolinecarbonyl)-L-leucinyl]amino]-pyrrolidine Following the procedure of Example 74(b), except substituting 2-quinolinecarboxylic acid, the title compound was prepared: MS (ES+) (MH+) 537.3.

Example 76

Preparation of 1-(4-phenoxy)benzyl-(3S)-[[N$^\alpha$-(3,4-dimethoxybenzoyl)-L-leucinyl]amino]-pyrrolidine Following the procedure of Example 74(b), except substituting 3,4-dimethoxybenzoic acid, the title compound was prepared: MS (ES+) (MH+) 546.3.

Example 77

Preparation of 1-(4-phenoxy)benzyl-(3S)-[[N$^\alpha$-(benzofuran-2-carbonyl)-L-leucinyl]amino]-pyrrolidine Following the procedure of Example 74(b), except substituting benzofuran-2-carboxylic acid, the title compound was prepared: MS (ES+) (MH+) 526.4.

Example 78

Preparation of 1-(4-phenoxy)benzyl-(3S)-[[N$^\alpha$-(benzo[b]thiophene-2-carbonyl)-L-leucinyl]amino]-pyrrolidine Following the procedure of Example 74(b), except substituting benzo[b]thiophene-2-carboxylic acid, the title compound was prepared: MS (ES+) (MH+) 542.3.

Example 79

Preparation of 1-(4-fluoro)benzyl-(3S)-[[N$^\alpha$-(tert-butoxycarbonyl)-L-leucinyl]amino]-pyrrolidine Following the procedure of Example 60(d), except substituting 4-fluorobenzaldehyde, the title compound was prepared: MS (ES+) (MH+) 408.3.

Example 80

Preparation of 1-(4-fluoro)benzyl-(3S)-[[N$^\alpha$-(2-naphthylcarbonyl)-L-leucinyl]amino]-pyrrolidine a) 1-(4-fluoro)benzyl-(3S)-[[N$^\alpha$-L-leucinyl]amino]-pyrrolidine dihydrochloride The compound of Example 79 (508 mg, 1.25 mmol) was dissolved in 4.0 N HCl in dioxane (25 mL) and stirred at room temperature for 1 h. The solution was concentrated to a white solid and dried under high vacuum for 30 min to give the title compound: MS (ES+) (MH+) 308.3.

b) 1-(4-fluoro)benzyl-(3S)-[[N$^\alpha$-(2-naphthylcarbonyl)-L-leucinyl]amino]-pyrrolidine Following the procedure of Example 61(b), except substituting the compound of Example 80(a), the title compound was prepared: MS (ES+) (MH+) 462.3.

Example 81

Preparation of 1-(4-fluoro)benzyl-(3S)-[[N$^\alpha$-(benzo[b]thiophene-2-carbonyl)-L-leucinyl]amino]-pyrrolidine Following the procedure of Example 80(b), except substituting benzo[b]thiophene-2-carboxylic acid, the title compound was prepared: MS (ES+) (MH+) 468.3.

Example 82

Preparation of 1-(4-cyano)benzyl-(3S)-[[N$^\alpha$-(tert-butoxycarbonyl)-L-leucinyl]amino]-pyrrolidine Following the procedure of Example 60(d), except substituting 4-cyanobenzaldehyde, the title compound was prepared: MS (ES+) (MH+) 415.4.

Example 83

Preparation of 1-(4-cyano)benzyl-(3S)-[[N$^\alpha$-(2-naphthylcarbonyl)-L-leucinyl]amino]-pyrrolidine a) 1-(4-cyano)benzyl-(3S)-[[N$^\alpha$-L-leucinyl]amino]-pyrrolidine dihydrochloride The compound of Example 82 (512 mg, 1.23 mmol) was dissolved in 4.0 N HCl in dioxane (25 mL) and stirred at room temperature for 1 h. The solution was concentrated to a white solid and dried under high vacuum for 30 min to give the title compound: MS (ES+) (MH+) 315.4.

b) 1-(4-cyano)benzyl-(3S)-[[N$^\alpha$-(2-naphthylcarbonyl)-L-leucinyl]amino]-pyrrolidine Following the procedure of Example 61(b), except substituting the compound of Example 83(a), the title compound was prepared: MS (ES+) (MH+) 469.5.

Example 84

Preparation of 1-benzyl-(3S)-[[N$^\alpha$-(benzo[b]thiophene-2-carbonyl)-L-leucinyl]amino]-pyrrolidine a) 1-benzyl-(3S)-[[N$^\alpha$-(tert-butoxycarbonyl)amino]-pyrrolidine To a stirred solution of (3S)-(−)-3-(tert-butoxycarbonylamino)pyrrolidine (10 g, 53.7 mmol) in CH$_2$Cl$_2$ (125 mL) was added benzaldehyde (6.6 mL, 64.9 mmol). The reaction was stirred 2 h whereupon Na(OAc)$_3$ (25.05 g, 118.2 mmol) was added. After stirring overnight, small aliquots of 5% NaHCO$_3$ were added until foaming had ceased. The reaction mixture was diluted with CHCl$_3$ (150 mL) and washed with 5% NaHCO$_3$ and brine, then dried (MgSO$_4$), filtered, and concentrated. Column chromatography (silica gel, 1:1 EtOAc:hexane) gave 11.5 g of the title compound: MS (ES+) (MH+) 277.2.

b) 1-benzyl-(3S)-[[N$^\alpha$-(tert-butoxycarbonyl)-L-leucinyl]amino]-pyrrolidine The compound of Example 84(a) (11.0 g, 39.8 mmol) was dissolved in 4.0 N HCl in dioxane (300 mL) and stirred at room temperature for 1 h. The solution was concentrated to a white solid and dried under high vacuum. To a stirred solution of the residue in DMF (100 mL) was added N-methylmorpholine (13.1 mL, 119.1 mmol), HOBt (8.07 g, 59.7 mmol), Boc-Leucine hydrate (14.89 g, 59.7 mmol), and EDC (11.44 g, 59.7 mmol). The reaction was stirred overnight whereupon it was diluted with EtOAc (500 mL), and washed with 1:1 10% Na$_2$CO$_3$:brine (300 mL). The aqueous layer was washed with fresh EtOAc (150 mL), the combined organic layers were washed with 10% Na$_2$CO$_3$ and brine, then dried (MgSO$_4$), filtered, and concentrated. Column chromatography (silica gel, 1:2 EtOAc:hexane to 1:1 EtOAc:hexane) gave 13.5 g of the title compound: MS (ES+) (MH+) 390.4.

c) 1-benzyl-(3S)-[[N$^\alpha$-L-leucinyl]amino]-pyrrolidine dihydrochloride

The compound of Example 84(b) (11.6 g, 29.8 mmol) was dissolved in 4.0 N HCl in dioxane (300 mL) and stirred at room temperature for 1 h. The solution was concentrated to a white solid and dried under high vacuum to give the title compound: MS (ES+) (MH+) 290.4.

d) 1-benzyl-(3S)-[[N$^\alpha$-(benzo[b]thiophene-2-carbonyl)-L-leucinyl]amino]-pyrrolidine To a stirred solution of the compound of Example 84 (c) (109.2 mg, 0.30 mmol) in DMF (1 mL) was added N-methylmorpholine (100 uL, 0.91 mmol), HOBt (61.6 mg, 0.46 mmol), benzo[b]thiophene-2-carboxylic acid (80.8 mg, 0.45 mmol), and EDC (86.6 mg, 0.45 mmol). The reaction was stirred overnight whereupon it was partitioned between 50 mL each of EtOAc, 10% Na$_2$CO$_3$, and brine. The aqueous layer was washed with fresh EtOAc (50 mL), the combined organic layers were washed with 10% Na$_2$CO$_3$ and brine, then dried (MgSO$_4$), filtered, and concentrated. Column chromatography (silica gel, 4:1 EtOAc:hexane) gave 85.0 mg of the title compound: MS (ES+) (MH+) 450.0.

Example 85

Preparation of 1-benzyl-(3S)-[[N$^\alpha$-(3,4-dimethoxybenzoyl)-L-leucinyl]amino]-pyrrolidine Following the procedure of Example 84(d), except substituting 3,4-dimethoxybenzoic acid, the title compound was prepared: MS (ES+) (MH+) 454.4.

Example 86

Preparation 1-benzyl-(3S)-[[N$^\alpha$-(3-(2-dimethylaminoethoxy)-4-methoxybenzoyl)-L-leucinyl]amino]-pyrrolidine Following the procedure of Example 84(d), except substituting 3-(2-dimethylaminoethoxy)-4-methoxybenzoic acid, the title compound was prepared: MS (ES+) (MH+) 511.2.

Example 87

Preparation of 1-(4-nitro)benzyl-(3S)-[[N$^\alpha$-(2-naphthylcarbonyl)-L-leucinyl]amino]-pyrrolidine a) 1-benzyl-(3S)-[[N$^\alpha$-(2-naphthylcarbonyl)-L-leucinyl]amino]-pyrrolidine To a stirred solution of the compound of Example 84(c) (7.25 g, 20.0 mmol) in DMF (50 mL) was added N-methylmorpholine (6.60 mL, 60.0 mmol), HOBt (4.05 g, 30.0 mmol), 2-naphthoic acid (5.17 g, 30.0 mmol), and EDC (5.76 g, 30.1 mmol). The reaction was stirred overnight whereupon it was partitioned between EtOAc (300 mL), 10% Na$_2$CO$_3$ (150 mL), and brine (150 mL). The aqueous layer was washed with fresh EtOAc (150 mL), the combined organic layers were washed with 10% Na$_2$CO$_3$ and brine, then dried (MgSO$_4$), filtered, and concentrated. Column chromatography (silica gel, 3:1 EtOAc:hexane to EtOAc) gave 5.7 g of the title compound: MS (ES+) (MH+) 444.0.

b) (3S)-[[N$^\alpha$-(2-naphthylcarbonyl)-L-leucinyl]amino]-pyrrolidine

To a stirred suspension of the compound of Example 87(a) (2.22 g, 5.00 mmol) in anhydrous dichloroethane (10 mL) at 0° C., in an oven-dried flask under an Argon atmosphere, was added a solution of 1-chloroethyl chloroformate (600 uL, 5.56 mmol) in dichloroethane, drop-wise over 10 min. After stirring at 0° C. for 15 min, the reaction was heated to reflux for 1.5 h, cooled to room temperature, and concentrated. The residue was dissolved in anhydrous MeOH (10 mL) and heated to reflux overnight, The reaction was cooled to room temperature, whereupon it was concentrated, dissolved in H$_2$O, and basified to pH 9–9.5 by the addition of solid Na$_2$CO$_3$. The aqueous solution was extracted with CHCl$_3$ (2×100 mL), the combined organic layers were washed with brine, then dried (MgSO$_4$), filtered, and concentrated. Column chromatography (silica gel, 10:90 MeOH:CHCl$_3$ to 10:90:0.1 MeOH:CHCl$_3$:NH$_4$OH) gave 0.82 g of the title compound: MS (ES+) (MH+) 354.3.

c) 1-(4-nitro)benzyl-(3S)-[[N$^\alpha$-(2-naphthylcarbonyl)-L-leucinyl]amino]-pyrrolidine To a stirred solution of the compound of Example 87(b) (106.5 mg, 0.30 mmol) in CH$_2$Cl$_2$ (1 mL) was added 4-nitrobenzaldehyde (55.5 mg, 0.37 mmol). The reaction was stirred 1.5 h whereupon Na(OAc)$_3$ (141.3 mg, 0.67 mmol) added. After stirring overnight, the reaction mixture was diluted with CHCl$_3$ (100 mL) and washed with 5% NaHCO$_3$ and brine, then dried (MgSO$_4$), filtered, and concentrated. Column chromatography (silica gel, EtOAc) gave 88.0 mg of the title compound: MS (ES+) (MH+) 489.3.

Example 88

Preparation of 1-(4-(N,N-dimethylamino)benzyl-(3S)-[[N$^\alpha$-(2-naphthylcarbonyl)-L-leucinyl]amino]-pyrrolidine Following the procedure of Example 87(c), except substituting 4-(N,N-dimethylamino)benzaldehyde, the title compound was prepared: MS (ES+) (MH+) 487.1.

Example 89

Preparation of 1-(4-methoxy)benzyl-(3S)-[[N$^\alpha$-(2-naphthylcarbonyl)-L-leucinyl]amino]-pyrrolidine Following the procedure of Example 87(c), except substituting p-anisaldehyde, the title compound was prepared: MS (ES+) (MH+) 474.4.

Example 90

Preparation of 1-(4-pyridyl)methyl-(3S)-[[N$^\alpha$-(2-naphthylcarbonyl)-L-leucinyl]amino]-pyrrolidine Following the procedure of Example 87(c), except substituting 4-pyridinecarboxaldehyde, the title compound was prepared: MS (ES+) (MH+) 445.4.

Example 91

Preparation of 1-(4-carboxymethyl)benzyl-(3S)-[[N$^\alpha$-(2-naphthylcarbonyl)-L-leucinyl]amino]-pyrrolidine Following the procedure of Example 87(c), except substituting methyl-4-formylbenzoate, the title compound was prepared: MS (ES+) (MH+) 502.3.

Example 92

Preparation of 1-(3,4-methylenedioxy)benzyl-(3S)-[[N$^\alpha$-(2-naphthylcarbonyl)-L-leucinyl]amino]-pyrrolidine Following the procedure of Example 87(c), except substituting piperonal, the title compound was prepared: MS (ES+) (MH+) 488.2.

Example 93

Preparation of 1-(2-naphthyl)methyl-(3S)-[[N$^\alpha$-(2-naphthylcarbonyl)-L-leucinyl]amino]-pyrrolidine Following the procedure of Example 87(c), except substituting 2-naphthaldehyde, the title compound was prepared: MS (ES+) (MH+) 494.2.

Example 94

Preparation of 1-(3-indolyl)methyl-(3S)-[[N$^\alpha$-(2-naphthylcarbonyl)-L-leucinyl]amino]-pyrrolidine Following the procedure of Example 87(c), except substituting indole-3-carboxaldehyde, the title compound was prepared: MS (ES+) (MH+) 483.4.

Example 95

Preparation of 1-(2-quinolinyl)methyl-(3S)-[[N$^\alpha$-(2-naphthylcarbonyl)-L-leucinyl]amino]-pyrrolidine Following the procedure of Example 87c), except substituting quinoline-2-carboxaldehyde, the title compound was prepared: MS (ES+) (MH+) 495.4.

Example 96

Preparation of 1-(3-quinolinyl)methyl-(3S)-[[N$^\alpha$-(2-naphthylcarbonyl)-L-leucinyl]amino]-pyrrolidine Following the procedure of Example 87(c), except substituting quinoline-3-carboxaldehyde, the title compound was prepared: MS (ES+) (MH+) 495.3.

Example 97

Preparation of 1-(1-naphthyl)methyl-(3S)-[[N$^\alpha$-(2-naphthylcarbonyl)-L-leucinyl]amino]-pyrrolidine Following the procedure of Example 87(c), except substituting 1-naphthaldehyde, the title compound was prepared: MS (ES+) (MH+) 494.3.

Example 98

Preparation of 1-(4-quinolinyl)methyl-(3S)-[[N$^\alpha$-(2-naphthylcarbonyl)-L-leucinyl]amino]-pyrrolidine Following the procedure of Example 87(c), except substituting quinoline-4-carboxaldehyde, the title compound was prepared: MS (ES+) (MH+) 495.3.

Example 99

Preparation 1-(3-pyrrolyl)methyl-(3S)-[[N$^\alpha$-(2-naphthylcarbonyl)-L-leucinyl]amino]-pyrrolidine Following the procedure of Example 87(c), except substituting pyrrole-2-carboxaldehyde, the title compound was prepared: MS (ES+) (MH+) 433.3.

Example 100

Preparation of 1-(3-pyridyl)methyl-(3S)-[[N$^\alpha$-(2-naphthylcarbonyl)-L-leucinyl]amino]-pyrrolidine Following the procedure of Example 87(c), except substituting pyridine-3-carboxaldehyde, the title compound was prepared: MS (ES+) (MH+) 445.2.

Example 101

Preparation of 1-(2-pyridyl)methyl-(3S)-[[N$^\alpha$-(2-naphthylcarbonyl)-L-leucinyl]amino]-pyrrolidine Following the procedure of Example 87(c), except substituting pyridine-2-carboxaldehyde, the title compound was prepared: MS (ES+) (MH+) 445.1.

Example 102

Preparation of 1-(3-nitro)benzyl-(3S)-[[N$^\alpha$-(2-naphthylcarbonyl)-L-leucinyl]amino]-pyrrolidine Following the procedure of Example 87(c), except substituting 3-nitrobenzaldehyde, the title compound was prepared: MS (ES+) (MH+) 489.3.

Example 103

Preparation of 1-(4-acetamido)benzyl-(3S)-[[N$^\alpha$-(2-naphthylcarbonyl)-L-leucinyl]amino]-pyrrolidine a) 1-(2,2,2-trichloroethyl)carbonyl-(3S)-[[N$^\alpha$-(tert-butoxycarbonyl)amino]-pyrrolidine To a stirred solution of (3S)-(−)-3-(tert-butoxycarbonylamino)pyrrolidine (10 g, 53.7 mmol) in CH$_2$Cl$_2$ (150 mL) at 0° C. was added N-methylmorpholine (6.50 mL, 59.1 mmol), and 2,2,2-trichloroethyl chloroformate (8.20 mL, 59.6 mmol). After stirring overnight, gradually warming to room temperature, the reaction mixture was diluted with CHCl$_3$ (250 mL) and washed with 5% NaHCO$_3$, H$_2$O, 1N HCl, H$_2$O, and brine, then dried (MgSO$_4$), filtered, and concentrated to give 19.96 g of the title compound: $^1$H-NMR (400 MHz, CDCl$_3$): d (ppm) 4.74 (s, 2H); 4.66 (br m, 1H); 4.25 (br m, 1H); 3.72 (m, 1H); 3.56 (m, 2H); 3.33 (m, 1H); 2.19 (m, 1H); 1.87 (m, 1H); 1.45 (s, 9H).

b) 1-(2,2,2-trichloroethyl)carbonyl-(3S)-[[N$^\alpha$-(tert-butoxycarbonyl)-L-leucinyl]amino]-pyrrolidine The compound of Example 103(a) (19.9 g) was dissolved in 4.0 N HCl in dioxane (400 mL) and stirred at room temperature for 1 h. The solution was concentrated to a white solid and stored under high vacuum. To a stirred solution of the residue in DMF (200 mL) was added N-methylmorpholine (8.90 mL, 80.9 mmol), HOBt (10.88 g, 80.5 mmol), Boc-Leucine hydrate (20.10 g, 80.6 mmol), and EDC (15.45 g, 80.7 mmol). The reaction was stirred overnight whereupon it was concentrated to remove most of the DMF, then diluted with EtOAc (300 mL), and washed with brine (150 mL). The aqueous layer was washed with fresh EtOAc (100 mL), the combined organic layers were washed with 1N HCl, H$_2$O, 10% Na$_2$CO$_3$, H$_2$O, and brine, then dried (MgSO$_4$), filtered, and concentrated to give 24.64 g of the title compound: $^1$H-NMR (400 MHz, CDCl$_3$): d (ppm) 6.55 (br m, 1H); 4.88 (m, 1H); 4.76 (s, 2H); 4.48 (m, 1H); 4.03 (m, 1H); 3.75 (m, 1H); 3.58 (m, 2H); 3.33 (m, 1H); 2.19 (m, 1H); 1.88 (m, 1H); 1.64 (m, 2H); 1.49 (m, 1H); 1.44 (s, 9H); 0.93 (m, 6H).

c) 1-(2,2,2-trichloroethyl)carbonyl-(3S)-[[N$^\alpha$-L-leucinyl]amino]-pyrrolidine hydrochloride The compound of Example 103 (b) (24.5 g) was dissolved in 4.0 N HCl in dioxane (500 mL) and stirred at room temperature for 1 h. The solution was concentrated to a white solid and dried under high vacuum to give the title compound: MS (ES+) (MH+) 375.

d) 1-(2,2,2-trichloroethyl)carbonyl-(3S)-[[N$^\alpha$-(2-naphthylcarbonyl)-L-leucinyl]amino]-pyrrolidine To a stirred solution of the compound of Example 103(c) (10.28 g, 25.0 mmol) in DMF (75 mL) was added N-methylmorpholine (4.2 mL, 38.2 mmol), HOBt (5.07 g, 37.5 mmol), 2-naphthoic acid (6.46 g, 37.5 mmol), and EDC (7.18 g, 37.5 mmol). The reaction was stirred overnight whereupon it was concentrated to remove most of the DMF, then partitioned between EtOAc (300 mL), 1N HCl (150 mL), and brine (150 mL). The aqueous layer was washed with fresh EtOAc (150 mL), the combined organic layers were washed with 1N HCl, H$_2$O, 10% Na$_2$CO$_3$, H$_2$O, and brine, then dried (MgSO$_4$), filtered, and concentrated. Column chromatography (silica gel, 1:2 EtOAc:hexane to 1:1 EtOAc:hexane) gave 9.74 g of the title compound: MS (ES+) (MH+) 528.1.

e) (3S)-[[N$^\alpha$-(2-naphthylcarbonyl)-L-leucinyl]amino]-pyrrolidine

To a stirred solution of the compound of Example 103(d) (9.65 g) in THF (75 mL) was added a solution of 1N NH$_4$OAc (pH 7–7.5, 15 mL), followed by Zn powder (9.53 g). The reaction was stirred for 5 h at room temperature whereupon fresh Zn (4 g) was added and the reaction was stirred overnight. The slurry was filtered through a pad of Celite, followed by several THF washes. The combined filtrates were concentrated to remove THF, diluted with CHCl$_3$ (300 mL), washed with 10% Na$_2$CO$_3$ and brine, then dried (MgSO$_4$), filtered, and concentrated. Column chromatography (silica gel, 10:90 MeOH:CHCl$_3$ to 10:90:0.25 MeOH:CHCl$_3$:NH$_4$OH) gave 5.71 g of the title compound: MS (ES+) (MH+) 354.2.

f) 1-(4-acetamido)benzyl-(3S)-[[N$^\alpha$-(2-naphthylcarbonyl)-L-leucinyl]amino]-pyrrolidine To a stirred solution of the compound of Example 103(e) (106.5 mg, 0.3 mmol) in CH$_2$Cl$_2$ (1 mL) was added 4-acetamidobenzaldehyde (59.7 mg, 0.37 mmol). The reaction was stirred 2 h whereupon Na(OAc)$_3$ (140.0 mg, 0.66 mmol) was added. After stirring overnight, the reaction mixture was diluted with CHCl$_3$ (100 mL) and washed with 5% NaHCO$_3$ and brine, then dried (MgSO$_4$), filtered, and concentrated. Column chromatography (silica gel, 5:95 MeOH:EtOAc) gave 105.1 mg of the title compound: MS (ES+) (MH+) 501.4.

Example 104

Preparation of 1-(3-cyano)benzyl-(3S)-[[N$^\alpha$-(2-naphthylcarbonyl)-L-leucinyl]amino]-pyrrolidine Following the procedure of Example 103(f), except substituting 3-cyanobenzaldehyde, the title compound was prepared: MS (ES+) (MH+) 469.2.

Example 105

Preparation of 1-(3-fluoro)benzyl-(3S)-[[N$^\alpha$-(2-naphthylcarbonyl)-L-leucinyl]amino]-pyrrolidine Following the procedure of Example 103(f), except substituting 3-fluorobenzaldehyde, the title compound was prepared: MS (ES+) (MH+) 462.3.

Example 106

Preparation of 1-(3-phenoxy)benzyl-(3S)-[[N$^\alpha$-(2naphthylcarbonyl)-L-leucinyl]amino]-pyrrolidine Following the procedure of Example 103(f), except substituting 3-phenoxybenzaldehyde, the title compound was prepared: MS (ES+) (MH+) 536.3.

Example 107

Preparation of 1-(4-chloro)benzyl-(3S)-[[N$^\alpha$-(2-naphthylcarbonyl)-L-leucinyl]amino]-pyrrolidine Following the procedure of Example 103(f), except substituting 4-chlorobenzaldehyde, the title compound was prepared: MS (ES+) (MH+) 478.3.

Example 108

Preparation of 1-(4-trifluoromethyl)benzyl-(3S)-[[N$^\alpha$-(2-naphthylcarbonyl)-L-leucinyl]amino]-pyrrolidine Following the procedure of Example 103(f), except substituting 4-(trifluoromethyl)benzaldehyde, the title compound was prepared: MS (ES+) (MH+) 512.3.

Example 109

Preparation of 1-(3-trifluoromethyl)benzyl-(3S)-[[N$^\alpha$-(2-naphthylcarbonyl)-L-leucinyl]amino]-pyrrolidine Following the procedure of Example 103(f), except substituting 3-(trifluoromethyl)benzaldehyde, the title compound was prepared: MS (ES+) (MH+) 512.2.

Example 110

Preparation of 1-(4-(3-(N,N-dimethylamino)propoxy)benzyl-(3S)-[[N$^\alpha$-(2-naphthylcarbonyl)-L-leucinyl]amino]-pyrrolidine Following the procedure of Example 103(f), except substituting 4-(3-dimethylaminopropoxy)benzaldehyde, the title compound was prepared: MS (ES+) (MH+) 545.2.

Example 111

Preparation of 1-(4-(isopropyl)benzyl-(3S)-[[N$^\alpha$-(2-naphthylcarbonyl)-L-leucinyl]amino]-pyrrolidine Following the procedure of Example 103(f), except substituting 4-isopropylbenzaldehyde, the title compound was prepared: MS (ES+) (MH+) 486.4.

Example 112

Preparation of 1-(2-benzofuranyl)methyl-(3S)-[[N$^\alpha$-(2-naphthylcarbonyl)-L-leucinyl]amino]-pyrrolidine Following the procedure of Example 103(f), except substituting benzofuran-2-carboxaldehyde, the title compound was prepared: MS (ES+) (MH+) 484.2.

Example 113

Preparation of 1-(2-(3-methylbenzo[b]thiophenyl)methyl-(3S)-[[N$^\alpha$-(2-naphthylcarbonyl)-L-leucinyl]amino]-pyrrolidine Following the procedure of Example 103(f), except substituting 3-methylbenzo[b]thiophene-2-carboxaldehyde, the title compound was prepared: MS (ES+) (MH+) 514.2.

Example 114

Preparation of 1-(2-furanyl)methyl-(3S)-[[N$^\alpha$-(2-naphthylcarbonyl)-L-leucinyl]amino]-pyrrolidine Following the procedure of Example 103(f), except substituting furan-2-carboxaldehyde, the title compound was prepared: MS (ES+) (MH+) 434.1.

Example 115

Preparation of 1-(3-furanyl)methyl-(3S)-[[N$^\alpha$-(2-naphthylcarbonyl)-L-leucinyl]amino]-pyrrolidine Following the procedure of Example 103(f), except substituting furan-3-carboxaldehyde, the title compound was prepared: MS (ES+) (MH+) 434.3.

Example 116

Preparation of SB 1-(2-thiophenyl)methyl-(3S)-[[N$^\alpha$-(2-naphthylcarbonyl)-L-leucinyl]amino]-pyrrolidine Following the procedure of Example 103(f), except substituting thiophene-3-carboxaldehyde, the title compound was prepared: MS (ES+) (MH+) 450.3.

Example 117

Preparation of 1-(2-nitro)benzyl-(3S)-[[N$^\alpha$-(2-naphthylcarbonyl)-L-leucinyl]amino]-pyrrolidine Following the procedure of Example 103(f), except substituting 2-nitrobenzaldehyde, the title compound was prepared: MS (ES+) (MH+) 489.3.

Example 118

Preparation of 1-(3-thiophenyl)methyl-(3S)-[[N$^\alpha$-(2-naphthylcarbonyl)-L-leucinyl]amino]-pyrrolidine Following the procedure of Example 103(f), except substituting thiophene-2-carboxaldehyde, the title compound was prepared: MS (ES+) (MH+) 450.2.

Example 119

Preparation of 1-(3,4-diomethoxy)benzyl-(3S)-[[N$^\alpha$-(2-naphthylcarbonyl)-L-leucinyl]amino]-pyrrolidine Following the procedure of Example 103(f), except substituting 3,4-dimethoxybenzaldehyde, the title compound was prepared: MS (ES+) (MR+) 504.2.

Example 120

Preparation of 1-(5-nitro-3-furanyl)methyl-(3S)-[[N$^\alpha$-(2-naphthylcarbonyl)-L-leucinyl]amino]-pyrrolidine Following the procedure of Example 103(f), except substituting 5-nitrofuran-2-carboxaldehyde, the title compound was prepared: MS (ES+) (MH+) 479.1.

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

What is claimed is:

1. A compound according to formula (Ia):

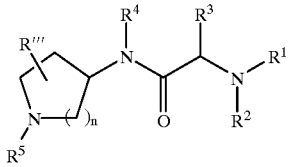

wherein:

R¹ is R", R"C(O), R"C(S), R"SO₂, R"OC(O), R"R'NC(O), or R"R'NC(S);

R² is H, $C_{1-6}$alkyl, $C_{2-6}$alkenyl, Ar-$C_{0-6}$alkyl, or Het-$C_{0-6}$alkyl;

R³ is H, $C_{2-6}$alkenyl, $C_{2-6}$alkynyl, Het, Ar or $C_{1-6}$alkyl optionally substituted by OR', SR', NR'₂, N(R')C(O)OR", CO₂R', CO₂NR'₂, N(C=NH)NH₂, Het or Ar;

R⁴ is H, $C_{1-6}$alkyl, $C_{2-6}$alkenyl, Ar-$C_{0-6}$alkyl, or Het-$C_{0-6}$alkyl;

R⁵ is

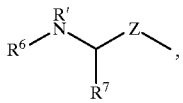

Ar-$C_{0-6}$alkyl, Het-$C_{0-6}$alkyl, adamantyl-C(O)—, Ar-C(O)—, or Het-C(O)—;

R⁶ is R", R"C(O), R"C(S), R"SO₂, R"OC(O), R"R'NC(O), R"R'NC(S),or R"OC(O)NR'CH(R*)C(O);

R⁷ is $C_{3-6}$cycloalkyl-$C_{0-6}$alkyl, Ar-$C_{0-6}$alkyl, Het-$C_{0-6}$alkyl, Ar-$C_{0-6}$alkoxy, Het-$C_{0-6}$alkoxy, or $C_{1-6}$alkyl optionally substituted by OR', SR', NR'₂, N(R')C(O)OR", CO₂R', CO₂NR'₂, N(C=NH)NH₂, Het or Ar;

R* is H, $C_{1-6}$alkyl, $C_{2-6}$alkenyl, $C_{3-6}$cycloalkyl-$C_{0-6}$-alkyl, Ar-$C_{0-6}$alkyl, Het-$C_{0-6}$alkyl;

each R' independently is H, $C_{1-6}$alkyl, $C_{2-6}$alkenyl, Ar-$C_{0-6}$ alkyl, or Het-$C_{0-6}$alkyl;

each R" independently is $C_{1-6}$alkyl, $C_{3-6}$cycloalkyl-$C_{0-6}$-alkyl, Ar-$C_{0-6}$alkyl, or Het-$C_{0-6}$alkyl;

R''' is H, $C_{1-6}$alkyl, $C_{3-6}$cycloalkyl-$C_{0-6}$alkyl, Ar-$C_{0-6}$alkyl, or Het-$C_{0-6}$alkyl;

Z is C(O) or CH₂; and n is 1, 2 or 3;

or a pharmaceutically acceptable salt thereof.

2. A compound according to claim 1 wherein R⁴ and R''' are each H.

3. A compound according to claim 1 wherein R³ is $C_{1-6}$alkyl.

4. A compound according to claim 3 wherein R³ is i-butyl.

5. A compound according to claim 1 wherein Y is NR¹R², in which R² is H and R¹ is R"C(O) or R"OC(O), and R" in said R¹ group is $C_{1-6}$alkyl, Ar-$C_{0-6}$alkyl or Het-$C_{0-6}$alkyl.

6. A compound according to claim 5 wherein R" in said R¹ group is tert-butyl,

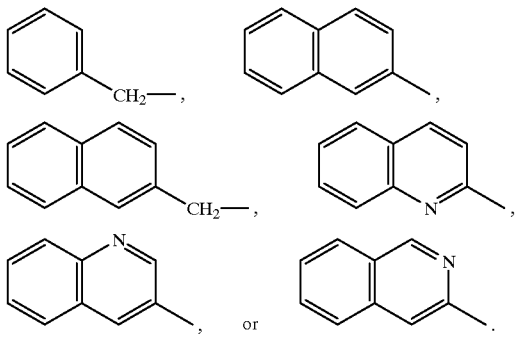

7. A compound according to claim 1 wherein n is 1 or 2.

8. A compound according to claim 7 wherein n is 1.

9. A compound according to claim 1 wherein R⁵ is benzyl or

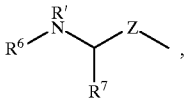

in which R' is H, R⁷ is $C_{1-6}$alkyl, R⁶ is R"OC(O) and Z is CH₂.

10. A compound according to claim 9 wherein, in said R⁵ group, R⁷ is i-butyl and R" is benzyl.

11. A compound according to claim 1 of the formula (Ib):

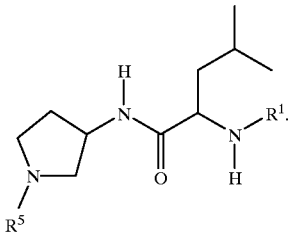

12. A compound according to claim 1 of the formula (Ic):

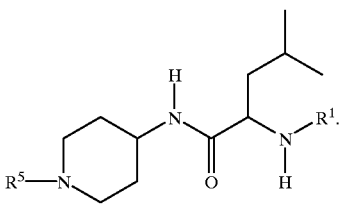

13. A compound which is:

3-[[N^α-(2-quinolinecarbonyl)-L-leucinyl]amino]-1-[(2S)-4-methyl-2-[[(benzyloxycarbonyl)amino]pentyl]-pyrrolidine;

1-benzyl-3-[[N^α-(2-quinolinecarbonyl)-L-leucinyl]amino]-pyrrolidine;

3-[[N^α-(2-naphthylcarbonyl)-L-leucinyl]amino]-1-[(2S)-4-methyl-2-[[(benzyloxycarbonyl)amino]pentyl]-pyrrolidine;

1-benzyl-3-[[N^α-(2-naphthylcarbonyl)-L-leucinyl]amino]-pyrrolidine;

1-benzyl-(3S)-[[N$^\alpha$-(benzyloxycarbonyl)-L-leucinyl]amino]-pyrrolidine;
1-benzyl-(3S)-[[N$^\alpha$-(tert-butoxycarbonyl)-L-leucinyl]amino]-pyrrolidine;
(3S)-[[N$^\alpha$-(2-naphthylcarbonyl)-L-leucinyl]amino]-1-[(2S)-4-methyl-2-[[(benzyloxycarbonyl)amino]pentyl]-pyrrolidine;
(3R)-[[N$^\alpha$-(2-naphthylcarbonyl)-L-leucinyl]amino]-1-[(2S)-4-methyl-2-[[(benzyloxycarbonyl)amino]pentyl]-pyrrolidine;
1-benzyl-(3R)-[[N$^\alpha$-(2-naphthyl)acetyl-L-leucinyl]amino]-pyrrolidine;
1-benzyl-(3R)-[[N$^\alpha$-(2-naphthylcarbonyl)-L-leucinyl]amino]-pyrrolidine;
1-benzyl-(3R)-[[N$^\alpha$-(3-quinolinecarbonyl)-L-leucinyl]amino]-pyrrolidine;
1-benzyl-(3R)-[[N$^\alpha$-(2-quinolinecarbonyl)-L-leucinyl]amino]-pyrrolidine;
1-benzyl-(3R)-[[N$^\alpha$-(3-isoquinolinecarbonyl)-L-leucinyl]amino]-pyrrolidine;
1-benzyl-(3S)-[[N$^\alpha$-(2-naphthyl)acetyl-L-leucinyl]amino]-pyrrolidine;
1-benzyl-(3S)-[[N$^\alpha$-(2-naphthylcarbonyl)-L-leucinyl]amino]-pyrrolidine;
1-benzyl-(3S)-[[N$^\alpha$-(3-quinolinecarbonyl)-L-leucinyl]amino]-pyrrolidine;
1-benzyl-(3S)-[[N$^\alpha$-(2-quinolinecarbonyl)-L-leucinyl]amino]-pyrrolidine;
1-benzyl-(3S)-[[N$^\alpha$-(3-isoquinolinecarbonyl(-L-leucinyl]amino]-pyrrolidine;
1-benzyl-4-[[N$^\alpha$-(2-naphthylcarbonyl)-L-leucinyl]amino]-piperidine;
1-benzyl-4-[[N$^\alpha$-(2-quinolinecarbonyl)-L-leucinyl]amino]-piperidine;
1-benzyl-4-[[N$^\alpha$-(benzyloxycarbonyl)-L-leucinyl]amino]-piperidine;
1-[3-(2-pyridyl)phenyl[-2-ethyl-(3S)-[[N$^\alpha$-(2-naphthylcarbonyl)-L-leucinyl]amino]-pyrrolidine;
1-[3-(2-pyridyl)phenyl[-2-ethyl-(3S)-[[N$^\alpha$-(2-quinolinecarbonyl)-L-leucinyl]amino]-pyrrolidine;
1-[3-(2-pyridyl)phenyl[-2-ethyl-(3S)-[[N$^\alpha$-(3-isoquinolinecarbonyl)-L-leucinyl]amino]-pyrrolidine;
1-[3-(2-pyridyl)phenyl[-2-ethyl-(3R)-[[N$^\alpha$-(2-naphthylcarbonyl)-L-leucinyl]amino]-pyrrolidine;
1-[3-(2-pyridyl)phenyl[-2-ethyl-(3R)-[[N$^\alpha$-(2-isoquinolinecarbonyl)-L-leucinyl]amino]-pyrrolidine;
1-[3-(2-pyridyl)phenyl[-2-ethyl-(3R)-[[N$^\alpha$-(2-quinolinecarbonyl)-L-leucinyl]amino]-pyrrolidine;
1-(1-adamantanecarbonyl)-(3R)-[[N$^\alpha$-(4-pyridylmethoxycarbonyl)-L-leucinyl]amino]-pyrrolidine;
1-(1-adamantanecarbonyl)-(3S)-[[N$^\alpha$-(4-pyridylmethoxycarbonyl)-L-leucinyl]amino]-pyrrolidine;
(3R)-[[N$^\alpha$-(benzo[b]thiophene-2-carbonyl)-L-leucinyl]amino]-1-[(2S)-4-methyl-2-[[(benzyloxycarbonyl)amino]pentyl]-pyrrolidine;
(3R)-[[N$^\alpha$-(3,4-dimethoxybenzoyl)-L-leucinyl]amino]-1-[(2S)-4-methyl-2-[[(benzyloxycarbonyl)amino]pentyl]-pyrrolidine;
(3R)-[[N$^\alpha$-(benzofuran-2-carbonyl)-L-leucinyl]amino]-1-[(2S)-4-methyl-2-[[(benzyloxycarbonyl)amino]pentyl]-pyrrolidine;
(3R)-[[N$^\alpha$-(benzothiazole-6-carbonyl)-L-leucinyl]amino]-1-[(2S)-4-methyl-2-[[(benzyloxycarbonyl)amino]pentyl]-pyrrolidine;
(3R)-[[N$^\alpha$-(indole-2-carbonyl)-L-leucinyl]amino]-1-[(2S)-4-methyl-2-[[(benzyloxycarbonyl)amino]pentyl]-pyrrolidine;
(3R)-[[N$^\alpha$-(4-fluorobenzoyl)-L-leucinyl]amino]-1-[(2S)-4-methyl-2-[[(benzyloxycarbonyl)amino]pentyl]-pyrrolidine;
(3R)-[[N$^\alpha$-(4-methoxybenzoyl)-L-leucinyl]amino]-1-[(2S)-4-methyl-2-[[(benzyloxycarbonyl)amino]pentyl]-pyrrolidine;
(3R)-[[N$^\alpha$-(3,4-dichlorobenzoyl)-L-leucinyl]amino]-1-[(2S)-4-methyl-2-[[(benzyloxycarbonyl)amino]pentyl]-pyrrolidine;
(3R)-[[N$^\alpha$-(thiophene-2-carbonyl)-L-leucinyl]amino]-1-[(2S)-4-methyl-2-[[(benzyloxycarbonyl)amino]pentyl]-pyrrolidine;
(3R)-[[N$^\alpha$-(4-biphenylcarbonyl)-L-leucinyl]amino]-1-[(2S)-4-methyl-2-[[(benzyloxycarbonyl)amino]pentyl]-pyrrolidine;
(3R)-[[N$^\alpha$-(5-methoxybenzofuran-2-carbonyl)-L-leucinyl]amino]-1-[(2S)-4-methyl-2-[[(benzyloxycarbonyl)amino]pentyl]-pyrrolidine;
(3R)-[[N$^\alpha$-(5-chlorobenzofuran-2-carbonyl)-L-leucinyl]amino]-1-[(2S)-4-methyl-2-[[(benzyloxycarbonyl)amino]pentyl]-pyrrolidine;
(3R)-[[N$^\alpha$-(7-methoxybenzofuran-2-carbonyl)-L-leucinyl]amino]-1-[(2S)-4-methyl-2-[[(benzyloxycarbonyl)amino]pentyl]-pyrrolidine;
(3R)-[[N$^\alpha$-(3-chlorobenzo[b]thiophene-2-carbonyl)-L-leucinyl]amino]-1-[(2S)-4-methyl-2-[[(benzyloxycarbonyl)amino]pentyl]-pyrrolidine;
(3R)-[[N$^\alpha$-(3-(2-pyridyl)benzoyl)-L-leucinyl]amino]-1-[(2S)-4-methyl-2-[[(benzyloxycarbonyl)amino]pentyl]-pyrrolidine;
(3S)-[[N$^\alpha$-(benzo[b]thiophene-2-carbonyl)-L-leucinyl]amino]-1-[(2S)-4-methyl-2-[[(benzyloxycarbonyl)amino]pentyl]-pyrrolidine;
(3S)-[[N$^\alpha$-(3,4-dimethoxybenzoyl)-L-leucinyl]amino]-1-[(2S)-4-methyl-2-[[(benzyloxycarbonyl)amino]pentyl]-pyrrolidine;
(3S)-[[N$^\alpha$-(benzofuran-2-carbonyl)-L-leucinyl]amino]-1-[(2S)-4-methyl-2-[[(benzyloxycarbonyl)amino]pentyl]-pyrrolidine;
(3S)-[[N$^\alpha$-(benzothiazole-6-carbonyl)-L-leucinyl]amino]-1-[(2S)-4-methyl-2-[[(benzyloxycarbonyl)amino]pentyl]-pyrrolidine;
(3S)-[[N$^\alpha$-(indole-2-carbonyl)-L-leucinyl]amino]-1-[(2S)-4-methyl-2-[[(benzyloxycarbonyl)amino]pentyl]-pyrrolidine;
(3S)-[[N$^\alpha$-(4-fluorobenzoyl)-L-leucinyl]amino]-1-[(2S)-4-methyl-2-[[(benzyloxycarbonyl)amino]pentyl]-pyrrolidine;
(3S)-[[N$^\alpha$-(4-methoxybenzoyl)-L-leucinyl]amino]-1-[(2S)-4-methyl-2-[[(benzyloxycarbonyl)amino]pentyl]-pyrrolidine;
(3S)-[[N$^\alpha$-(3,4-dichlorobenzoyl)-L-leucinyl]amino]-1-[(2S)-4-methyl-2-[[(benzyloxycarbonyl)amino]pentyl]-pyrrolidine;
(3S)-[[N$^\alpha$-(thiophene-2-carbonyl)-L-leucinyl]amino]-1-[(2S)-4-methyl-2-[[(benzyloxycarbonyl)amino]pentyl]-pyrrolidine;
(3S)-[[N$^\alpha$-(4-biphenylcarbonyl)-L-leucinyl]amino]-1-[(2S)-4-methyl-2-[[(benzyloxycarbonyl)amino]pentyl]-pyrrolidine;
(3S)-[[N$^\alpha$-(5-methoxybenzofuran-2-carbonyl)-L-leucinyl]amino]-1-[(2S)-4-methyl-2-[[(benzyloxycarbonyl)amino]pentyl]-pyrrolidine;
(3S)-[[N-$^\alpha$-(5-chlorobenzofuran-2-carbonyl)-L-leucinyl]amino]-1-[(2S)-4-methyl-2-[[(benzyloxycarbonyl)amino]pentyl]-pyrrolidine;
(3S)-[[N$^\alpha$-(7-methoxybenzofuran-2-carbonyl)-L-leucinyl]amino]-1-[(2S)-4-methyl-2-[[(benzyloxycarbonyl)amino]pentyl]-pyrrolidine;

(3S)-[[N$^\alpha$-(3-chlorobenzo[b]thiophene-2-carbonyl)-L-leucinyl]amino]-1-[(2S)-4-methyl-2-[[(benzyloxycarbonyl)amino]pentyl]-pyrrolidine;
(3S)-[[N$^\alpha$-(3-(2-pyridyl)benzoyl)-L-leucinyl]amino]-1-[(2S)-4-methyl-2-[[(benzyloxycarbonyl)amino]pentyl]-pyrrolidine;
1-(4-phenyl)benzyl-(3S)-[[N$^\alpha$-(tert-butoxycarbonyl)-L-leucinyl]amino]-pyrrolidine;
1-(4-phenyl)benzyl-(3S)-[[N$^\alpha$-(2-naphthylcarbonyl)-L-leucinyl]amino]-pyrrolidine;
1-(4-phenyl)benzyl-(3S)-[[N$^\alpha$-(2-quinolinecarbonyl)-L-leucinyl]amino]-pyrrolidine;
1-(4-phenyl)benzyl-(3S)-[[N$^\alpha$-(3,4-dimethoxybenzoyl)-L-leucinyl]amino]-pyrrolidine;
1-(4-phenyl)benzyl-(3S)-[[N$^\alpha$-(benzofuran-2-carbonyl)-L-leucinyl]amino]-pyrrolidine;
1-(4-phenyl)benzyl-(3S)-[[N$^\alpha$-(benzo[b]thiophene-2-carbonyl)-L-leucinyl]amino]-pyrrolidine;
1-(4-phenyl)benzyl-(3S)-[[N$^\alpha$-(benzyloxycarbonyl)-L-leucinyl]amino]-pyrrolidine;
1-(2-phenyl)ethyl-(3S)-[[N$^\alpha$-(tert-butoxycarbonyl)-L-leucinyl]amino]-pyrrolidine;
1-(2-phenyl)ethyl-(3S)-[[N$^\alpha$-(2-naphthylcarbonyl)-L-leucinyl]amino]-pyrrolidine;
1-(2-phenyl)ethyl-(3S)-[[N$^\alpha$-(2-quinolinecarbonyl)-L-leucinyl]amino]-pyrrolidine;
1-(2-phenyl)ethyl-(3S)-[[N$^\alpha$-(benzo[b]thiophene-2-carbonyl)-L-leucinyl]amino]-pyrrolidine;
1-(2-phenyl)ethyl-(3S)-[[N$^\alpha$-(benzofuran-2-carbonyl)-L-leucinyl]amino]-pyrrolidine;
1-(2-phenyl)ethyl-(3S)-[[N$^\alpha$-(3-chlorobenzo[b]thiophene-2-carbonyl)-L-leucinyl]amino]-pyrrolidine;
1-(4-phenoxy)benzyl-(3S)-[[N$^\alpha$-(tert-butoxycarbonyl)-L-leucinyl]amino]-pyrrolidine;
1-(4-phenoxy)benzyl-(3S)-[[N$^\alpha$-(2-naphthylcarbonyl)-L-leucinyl]amino]-pyrrolidine;
1-(4-phenoxy)benzyl-(3S)-[[N$^\alpha$-(2-quinolinecarbonyl)-L-leucinyl]amino]-pyrrolidine;
1-(4-phenoxy)benzyl-(3S)-[[N$^\alpha$-(3,4-dimethoxybenzoyl)-L-leucinyl]amino]-pyrrolidine;
1-(4-phenoxy)benzyl-(3S)-[[N$^\alpha$-(benzofuran-2-carbonyl)-L-leucinyl]amino]-pyrrolidine
1-(4-phenoxy)benzyl-(3S)-[[N$^\alpha$-(benzo[b]thiophene-2-carbonyl)-L-leucinyl]amino]-pyrrolidine;
1-(4-fluoro)benzyl-(3S)-[[N$^\alpha$-(tert-butoxycarbonyl)-L-leucinyl]amino]-pyrrolidine;
1-(4-fluoro)benzyl-(3S)-[[N$^\alpha$-(2-naphthylcarbonyl)-L-leucinyl]amino]-pyrrolidine;
1-(4-fluoro)benzyl-(3S)-[[N$^\alpha$-(benzo[b]thiophene-2-carbonyl)-L-leucinyl]amino]-pyrrolidine;
1-(4-cyano)benzyl-(3S)-[[N$^\alpha$-(tert-butoxycarbonyl)-L-leucinyl]amino]-pyrrolidine;
1-(4-cyano)benzyl-(3S)-[[N$^\alpha$-(2-naphthylcarbonyl)-L-leucinyl]amino]-pyrrolidine;
1-benzyl-(3S)-[[N$^\alpha$-(benzo[b]thiophene-2-carbonyl)-L-leucinyl]amino]-pyrrolidine;
1-benzyl-(3S)-[[N$^\alpha$-(3,4-dimethoxybenzoyl)-L-leucinyl]amino]-pyrrolidine;
1-benzyl-(3S)-[[N$^\alpha$-(3-(2-dimethylaminoethoxy)-4-methoxybenzoyl)-L-leucinyl]amino]-pyrrolidine;
1-(4-nitro)benzyl-(3S)-[[N$^\alpha$-(2-naphthylcarbonyl)-L-leucinyl]amino]-pyrrolidine;
1-(4-(N,N-dimethylamino)benzyl-(3S)-[[N$^\alpha$-(2-naphthylcarbonyl)-L-leucinyl]amino]-pyrrolidine;
1-(4-methoxy)benzyl-(3S)-[[N$^\alpha$-(2-naphthylcarbonyl)-L-leucinyl]amino]-pyrrolidine;
1-(4-pyridyl)methyl-(3S)-[[N$^\alpha$-(2-naphthylcarbonyl)-L-leucinyl]amino]-pyrrolidine;
1-(4-carboxymethyl)benzyl-(3S)-[[N$^\alpha$-(2-naphthylcarbonyl)-L-leucinyl]amino]-pyrrolidine;
1-(3,4-methylenedioxy)benzyl-(3S)-[[N$^\alpha$-(2-naphthylcarbonyl)-L-leucinyl]amino]-pyrrolidine;
1-(2-naphthyl)methyl-(3S)-[[N$^\alpha$-(2-naphthylcarbonyl)-L-leucinyl]amino]-pyrrolidine;
1-(3-indolyl)methyl-(3S)-[[N$^\alpha$-(2-naphthylcarbonyl)-L-leucinyl]amino]-pyrrolidine;
1-(2-quinolinyl)methyl-(3S)-[[N$^\alpha$-(2-naphthylcarbonyl)-L-leucinyl]amino]-pyrrolidine;
1-(3-quinolinyl)methyl-(3S)-[[N$^\alpha$-(2-naphthylcarbonyl)-L-leucinyl]amino]-pyrrolidine;
1-(1-naphthyl)methyl-(3S)-[[N$^\alpha$-(2-naphthylcarbonyl)-L-leucinyl]amino]-pyrrolidine;
1-(4-quinolinyl)methyl-(3S)-[[N$^\alpha$-(2-naphthylcarbonyl)-L-leucinyl]amino]-pyrrolidine;
1-(3-pyrrolyl)methyl-(3S)-[[N$^\alpha$-(2-naphthylcarbonyl)-L-leucinyl]amino]-pyrrolidine;
1-(3-pyridyl)methyl-(3S)-[[N$^\alpha$-(2-naphthylcarbonyl)-L-leucinyl]amino]-pyrrolidine;
1-(2-pyridyl)methyl-(3S)-[[N$^\alpha$-(2-naphthylcarbonyl)-L-leucinyl]amino]-pyrrolidine;
1-(3-nitro)benzyl-(3S)-[[N$^\alpha$-(2-naphthylcarbonyl)-L-leucinyl]amino]-pyrrolidine;
1-(4-acetamido)benzyl-(3S)-[[N$^\alpha$-(2-naphthylcarbonyl)-L-leucinyl]amino]-pyrrolidine;
1-(3-cyano)benzyl-(3S)-[[N$^\alpha$-(2-naphthylcarbonyl)-L-leucinyl]amino]-pyrrolidine;
1-(3-fluoro)benzyl-(3S)-[[N$^\alpha$-(2-naphthylcarbonyl)-L-leucinyl]amino]-pyrrolidine;
1-(3-phenoxy)benzyl-(3S)-[[N$^\alpha$-(2-naphthylcarbonyl)-L-leucinyl]amino]-pyrrolidine;
1-(4-chloro)benzyl-(3S)-[[N$^\alpha$-(2-naphthylcarbonyl)-L-leucinyl]amino]-pyrrolidine;
1-(4-trifluoromethyl)benzyl-(3S)-[[N$^\alpha$-(2-naphthylcarbonyl)-L-leucinyl]amino]-pyrrolidine;
1-(3-trifluoromethyl)benzyl-(3S)-[[N$^\alpha$-(2-naphthylcarbonyl)-L-leucinyl]amino]-pyrrolidine;
1-(4-(3-(N,N-dimethylamino)propoxy)benzyl-(3S)-[[N$^\alpha$-(2-naphthylcarbonyl)-L-leucinyl]amino]-pyrrolidine;
1-(4-(isopropyl)benzyl-(3S)-[[N$^\alpha$-(2-naphthylcarbonyl)-L-leucinyl]amino]-pyrrolidine;
1-(2-benzofuranyl)methyl-(3S)-[[N$^\alpha$-(2-naphthylcarbonyl)-L-leucinyl]amino]-pyrrolidine;
1-(2-(3-methylbenzo[b]thiophenyl)methyl-(3S)-[[N$^\alpha$-(2-naphthylcarbonyl)-L-leucinyl]amino]-pyrrolidine;
1-(2-furanyl)methyl-(3S)-[[N$^\alpha$-(2-naphthylcarbonyl)-L-leucinyl]amino]-pyrrolidine;
1-(3-furanyl)methyl-(3S)-[[N$^\alpha$-(2-naphthylcarbonyl)-L-leucinyl]amino]-pyrrolidine;
1-(2-thiophenyl)methyl-(3S)-[[N$^\alpha$-(2-naphthylcarbonyl)-L-leucinyl]amino]-pyrrolidine;
1-(2-nitro)benzyl-(3S)-[[N$^\alpha$-(2-naphthylcarbonyl)-L-leucinyl]amino]-pyrrolidine;
-(3-thiophenyl)methyl-(3S)-[[N$^\alpha$-(2-naphthylcarbonyl)-L-leucinyl]amino]-pyrrolidine;
1-(3,4-dimethoxy)benzyl-(3S)-[[N$^\alpha$-(2-naphthylcarbonyl)-L-leucinyl]amino]-pyrrolidine; or
1-(5-nitro-3-furanyl)methyl-(3S)-[[N$^\alpha$-(2-naphthylcarbonyl)-L-leucinyl]amino]-pyrrolidine;

a pharmaceutically acceptable salt thereof.

14. A pharmaceutical composition comprising a compound according to claim 1 and a pharmaceutically acceptable carrier.

15. A method of inhibiting a cysteine protease which comprises administering a compound according to claim 1.

16. A method according to claim 15 wherein the cysteine protease is cathepsin K.

17. A method of inhibiting bone loss which comprises administering a compound according to claim 1.

18. A method of treating osteoporosis which comprises administering a compound according to claim 1.

19. A method of treating gingival or peridontal disease which comprises administering a compound according to claim 1.

20. A method of treating a disease characterized by excessive cartilage or matrix degradation which comprises administering a compound according to claim 1.

21. A method according to claim 20 wherein said disease is osteoarthritis or rheumatoid arthritis.

22. A process for preparing a compound of the formula (Ia) as defined in claim 1, which process comprises:

reacting a compound of the formula (II):

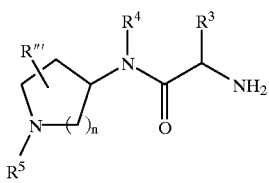
(II)

or a salt thereof, wherein R''', $R^3$, $R^4$, $R^5$ and n are as defined in formula (I) of claim 1, with any reactive functional groups protected, with:
(a) R"C(O)Cl, in which R" is as defined in formula (I) of claim 1; or
(b) R"C(O)OH, in which R" is as defined in formula (I) of claim 1, in the presence of EDC and HOBT; or
(c) R"C(O)H, in which R" is as defined in formula (I) of claim 1, followed by reduction; or
(d) R"OC(O)Cl, in which R" is as defined in formula (I) of claim 1, in the presence of base; or
(e) R"$SO_2$Cl, in which R" is as defined in formula (I) of claim 1, in the presence of base;

and thereafter removing any protecting groups and optionally forming a pharmaceutically acceptable salt.

23. A compound according to formula (II):

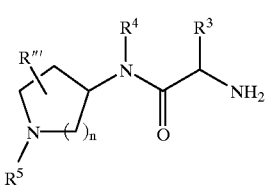
(II)

wherein:
$R^3$ is H, $C_{2-6}$alkenyl, $C_{2-6}$alkynyl, Het, Ar or $C_{1-6}$alkyl optionally substituted by OR', SR', NR'$_2$, N(R')C(O)OR", $CO_2$R', $CO_2$NR'$_2$, N(C=NH)$NH_2$, Het or Ar;

$R^4$ is H, $C_{1-6}$alkyl, $C_{2-6}$alkenyl, Ar-$C_{0-6}$alkyl, or Het-$C_{0-6}$alkyl;

$R^5$ is

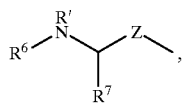,

Ar-$C_{0-6}$alkyl, Het-$C_{0-6}$alkyl, adamantyl-C(O)—, Ar-C(O)—, Het-C(O)— or;

$R^6$ is R", R"C(O), R"C(S), R"$SO_2$, R"OC(O), R"R'NC(O), R"R'NC(S), or R"OC(O)NR'CH(R*)C(O);

$R^7$ is $C_{3-6}$cycloalkyl-$C_{0-6}$alkyl, Ar-$C_{0-6}$alkyl, Het-$C_{0-6}$alkyl, Ar-$C_{0-6}$alkoxy, Het-$C_{0-6}$alkoxy, or $C_{1-6}$alkyl optionally substituted by OR', SR', NR'$_2$, N(R')C(O)OR", $CO_2$R', $CO_2$NR'$_2$, N(C=NH)$NH_2$, Het or Ar;

R* is H, $C_{1-6}$alkyl, $C_{2-6}$alkenyl, $C_{3-6}$cycloalkyl-$C_{0-6}$-alkyl, Ar-$C_{0-6}$alkyl, Het-$C_{0-6}$alkyl;

each R' independently is H, $C_{1-6}$alkyl, $C_{2-6}$alkenyl, Ar-$C_{0-6}$ alkyl, or Het-$C_{0-6}$alkyl;

each R" independently is $C_{1-6}$alkyl, $C_{3-6}$cycloalkyl-$C_{0-6}$-alkyl, Ar-$C_{0-6}$alkyl, or Het-$C_{0-6}$alkyl;

R'" is H, $C_{1-6}$alkyl, $C_{3-6}$cycloalkyl-$C_{0-6}$alkyl, Ar-$C_{0-6}$ alkyl, or Het-$C_{0-6}$alkyl;

Z is C(O) or $CH_2$; and n is 1, 2 or 3;

or a pharmaceutically acceptable salt thereof.

* * * * *